(12) United States Patent
Frisby et al.

(10) Patent No.: US 12,324,734 B2
(45) Date of Patent: *Jun. 10, 2025

(54) INTEGRATED LOADING AND STORAGE SYSTEM FOR IMPLANTABLE MEDICAL DEVICES

(71) Applicant: Medtronic CV Luxembourg S.a.r.l., Luxembourg (LU)

(72) Inventors: Paraic Frisby, Galway (IE); Niall Duffy, Galway (IE)

(73) Assignee: Medtronic CV Luxembourg S.A.R.L., Luxembourg (LU)

( * ) Notice: Subject to any disclaimer, the term of this patent is extended or adjusted under 35 U.S.C. 154(b) by 594 days.

This patent is subject to a terminal disclaimer.

(21) Appl. No.: 17/703,752

(22) Filed: Mar. 24, 2022

(65) Prior Publication Data

US 2022/0211480 A1    Jul. 7, 2022

Related U.S. Application Data

(63) Continuation of application No. 16/697,965, filed on Nov. 27, 2019, now Pat. No. 11,284,985.

(51) Int. Cl.
*A61F 2/24* (2006.01)
*A61F 2/00* (2006.01)
*A61F 2/95* (2013.01)

(52) U.S. Cl.
CPC .......... *A61F 2/0095* (2013.01); *A61F 2/2418* (2013.01); *A61F 2/2433* (2013.01); *A61F 2/9522* (2020.05)

(58) Field of Classification Search
CPC .... A61F 2/0095; A61F 2/2418; A61F 2/2436; A61F 2/9525
See application file for complete search history.

(56) References Cited

U.S. PATENT DOCUMENTS

| 8,876,894 B2* | 11/2014 | Tuval | A61F 2/2469 |
| | | | 623/2.14 |
| 11,284,985 B2* | 3/2022 | Frisby | A61F 2/2418 |
| 2003/0070682 A1* | 4/2003 | Wilson | A61F 2/2412 |
| | | | 128/207.16 |
| 2008/0071361 A1* | 3/2008 | Tuval | A61F 2/2418 |
| | | | 623/2.1 |

(Continued)

FOREIGN PATENT DOCUMENTS

| EP | 2710985 A2 | 3/2014 |
| WO | 2013016513 A1 | 1/2013 |
| WO | 2013045262 A1 | 4/2013 |

OTHER PUBLICATIONS

International Search Report and Written Opinion in International Application No. PCT/EP2020/081655, mailed Mar. 10, 2021.

*Primary Examiner* — Suzette J Gherbi

(57) ABSTRACT

A loading device includes a locking collar assembly including a proximal end, a distal end, and a loading channel formed between the proximal end and the distal end. The device also includes a loading funnel coupled to the distal end of the locking collar assembly at a proximal end of the loading funnel. The loading funnel is configured to store a collapsible medical device in a partially collapsed state within a tapered interior volume of the loading funnel. The tapered interior volume decreases in volume from a distal end of the loading funnel to the proximal end of the loading funnel.

23 Claims, 30 Drawing Sheets

(56) References Cited

U.S. PATENT DOCUMENTS

| | | | | |
|---|---|---|---|---|
| 2010/0094411 A1* | 4/2010 | Tuval | .................... | A61F 2/2427 623/2.11 |
| 2010/0137979 A1* | 6/2010 | Tuval | .................... | A61F 2/2469 623/2.11 |
| 2010/0256749 A1* | 10/2010 | Tran | ...................... | A61F 2/2436 206/370 |
| 2014/0081375 A1* | 3/2014 | Bardill | ...................... | A61F 2/95 623/1.15 |
| 2021/0228343 A1* | 7/2021 | Scheinblum | .......... | A61F 2/2427 |
| 2021/0316130 A1* | 10/2021 | Anderson | ........... | A61M 39/162 |

* cited by examiner

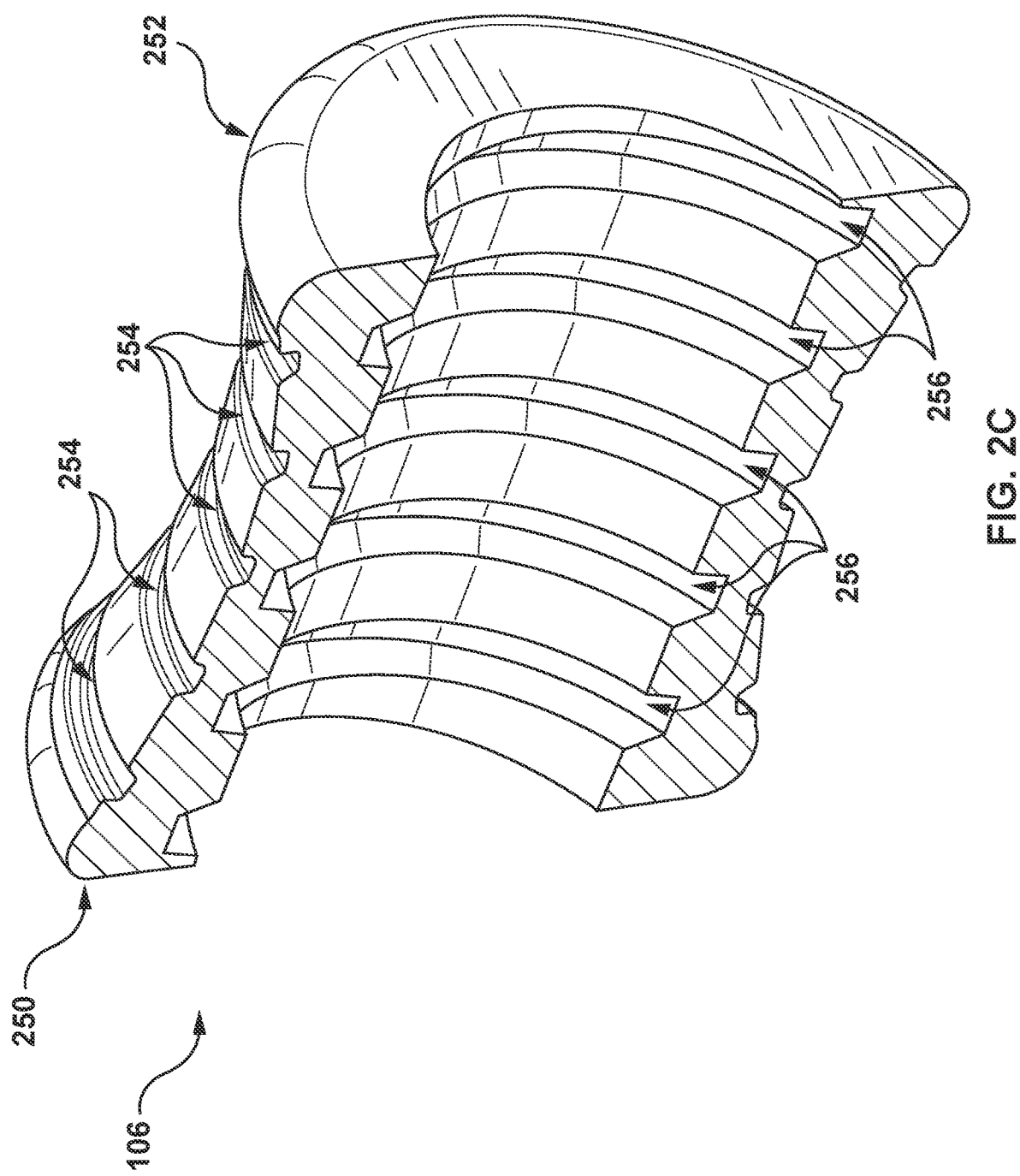

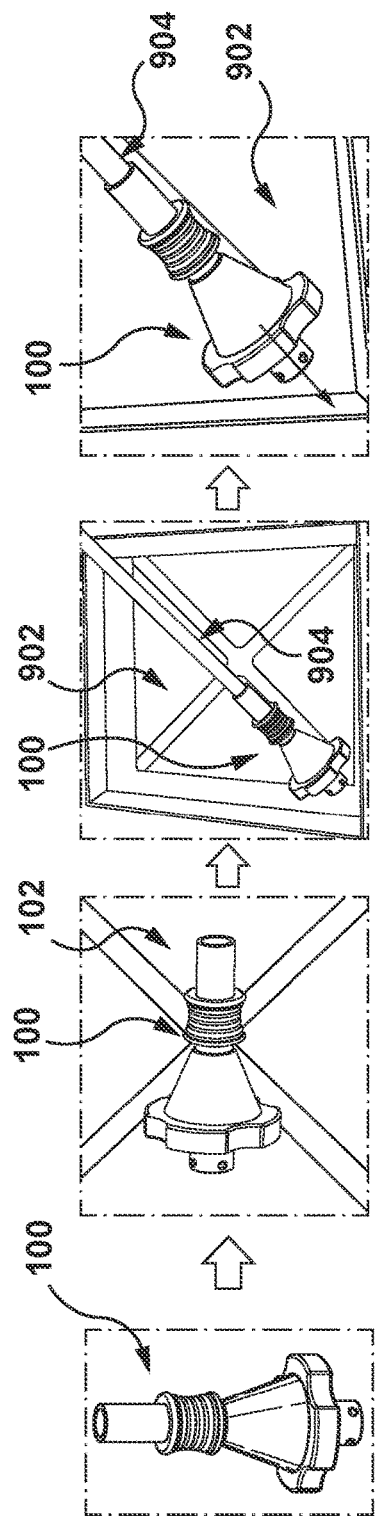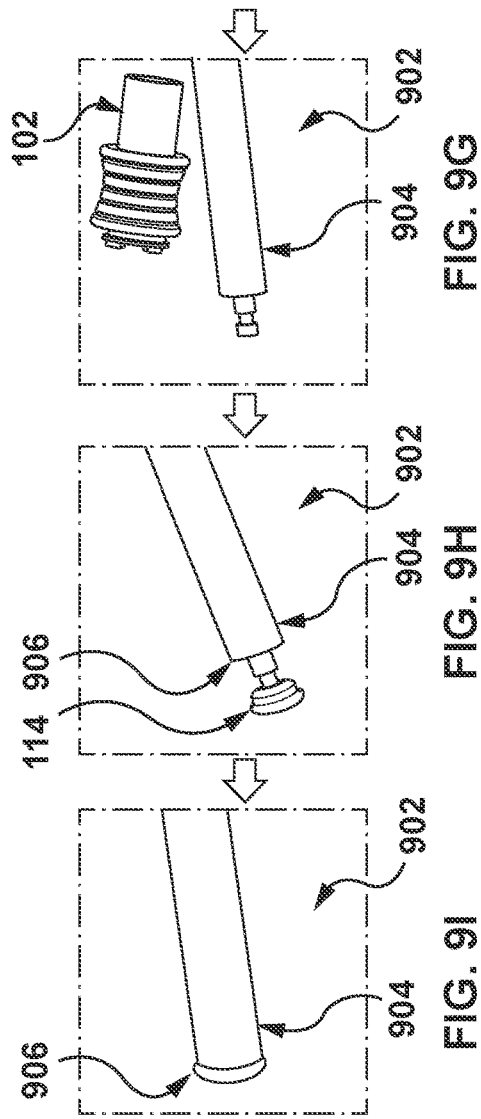

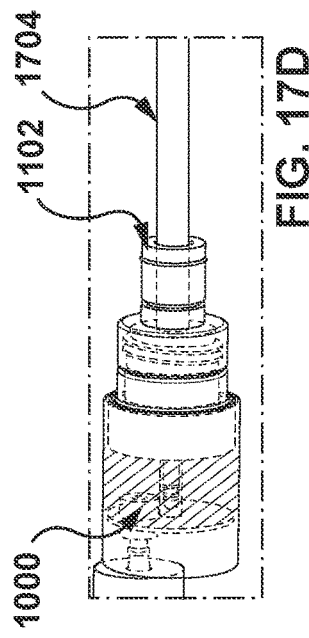
FIG. 17A
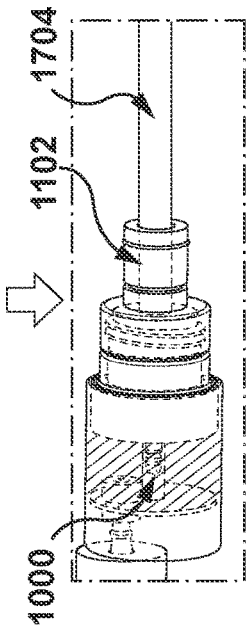
FIG. 17B
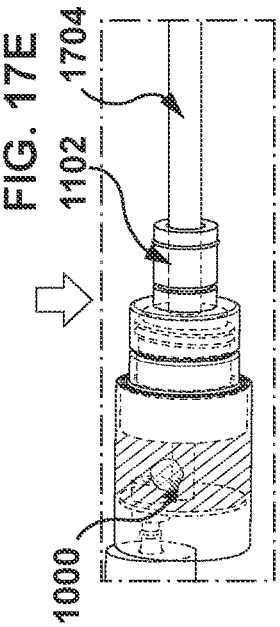
FIG. 17C
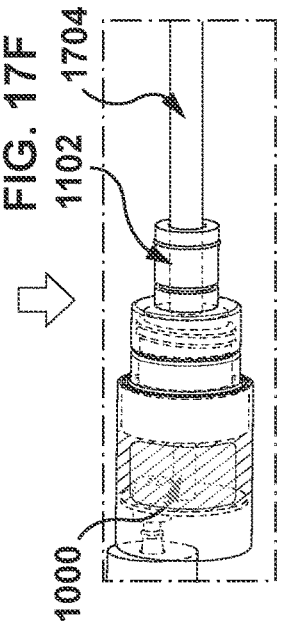
FIG. 17D
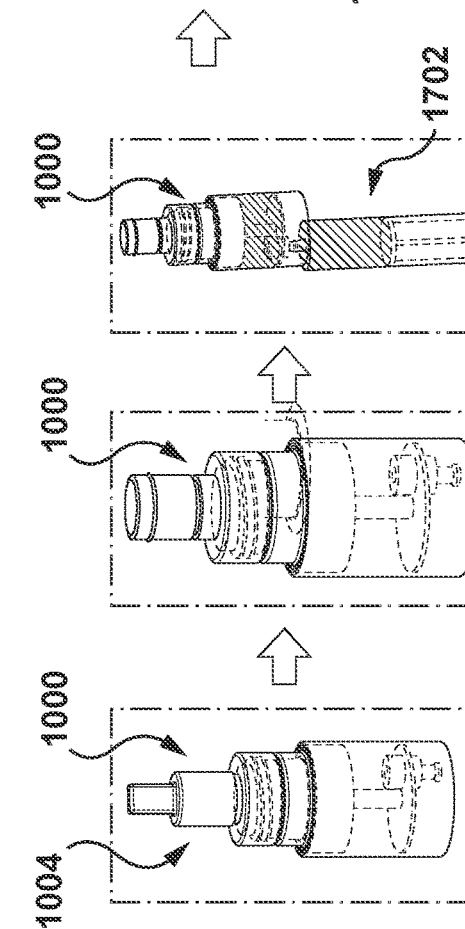
FIG. 17E
FIG. 17F
FIG. 17G
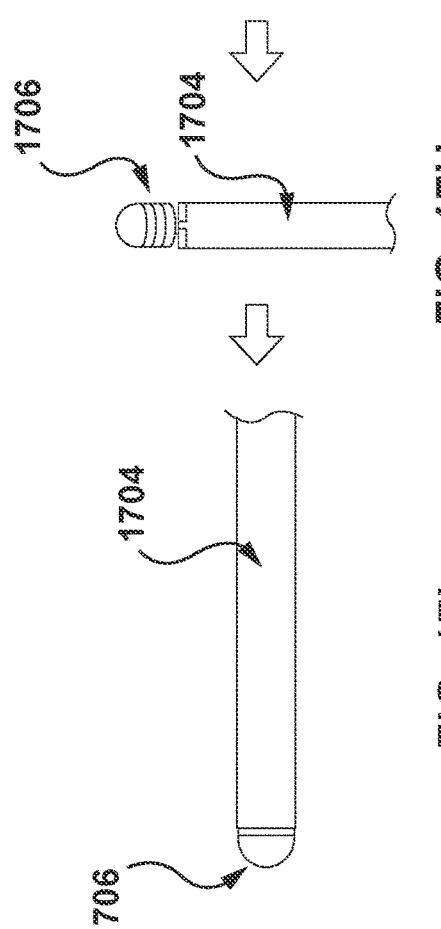
FIG. 17H
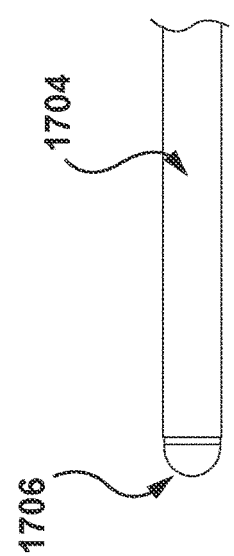
FIG. 17I

INTEGRATED LOADING AND STORAGE SYSTEM FOR IMPLANTABLE MEDICAL DEVICES

CROSS-REFERENCE TO RELATED APPLICATIONS

This application is a continuation of U.S. patent application Ser. No. 16/697,965, filed Nov. 27, 2019, the contents of which are incorporated by reference herein in their entirety.

FIELD

The present technology is generally related to loading and storage systems for medical devices.

BACKGROUND

Currently, implantable medical devices, such as stents, scaffolds, and other cardiac intervention devices that contain organic tissue, e.g., bovine and porcine, require onsite installation onto a delivery device. This is due to the need to store the implantable devices in conditions specific to preserve the organic tissue. Typically, a detailed process must be performed in order to install a medical device on a delivery device. The detailed process, however, can be cumbersome and costly due to the potential of damaging the implantable medical device during the installation.

SUMMARY

The techniques of this disclosure generally relate to a combination storage and loading system for loading an implantable medical device onto a delivery device and converting the implantable medical device from an uncompressed state to a compressed state.

In one aspect, the disclosure provides a device for storing medical devices and loading the medical devices onto delivery devices. The device includes a locking collar assembly including a proximal end, a distal end, and a loading channel formed between the proximal end and the distal end. The device also includes a loading funnel coupled to the distal end of the locking collar assembly at a proximal end of the loading funnel. The loading funnel is configured to store a collapsible medical device within a tapered interior volume of the loading funnel in a partially collapsed state. The tapered interior volume decreases in volume from a distal end of the loading funnel to the proximal end of the loading funnel. The device includes a retainer positioned with the loading channel at the distal end of the locking collar assembly and includes a connector configured to couple to a delivery device. The collapsible medical appliance is coupled to the retainer. The retainer maintains the collapsible medical device within the loading funnel prior to connection to the delivery device. The device further includes a nosecone pin coupled to the retainer and positioned within the tapered interior volume of the loading funnel. Additionally, the device includes a storage jar coupled to a distal end of the loading funnel. The storage jar is configured retain the collapsible medical device and the nosecone pin within the tapered interior volume of the loading funnel.

In another aspect, the present disclosure provides a device for storing medical devices and loading the medical devices onto delivery devices. The device includes a locking collar assembly including a proximal end, a distal end, and a loading channel formed between the proximal end and the distal end. The device also includes a loading funnel coupled to the distal end of the locking collar assembly at a proximal end of the loading funnel. The loading funnel is configured to store a collapsible medical device in a partially collapsed state within a tapered interior volume of the loading funnel. The tapered interior volume decreases in volume from a distal end of the loading funnel to the proximal end of the loading funnel. Further, the device includes a retainer positioned with the loading channel at the distal end of the locking collar assembly and includes a connector configured to couple to a delivery device. The collapsible medical device is coupled to the retainer. The retainer maintains the collapsible medical device within the loading funnel prior to connection to the delivery device. The device includes a nosecone pin coupled to the retainer and positioned within the tapered interior volume of the loading funnel. Additionally, the device includes a funnel cap coupled to the distal end of the loading funnel. The funnel cap is configured retain the collapsible medical device and the nosecone pin within the tapered interior volume of the loading funnel.

In another aspect, the disclosure provides a method for storing medical devices and loading the medical devices onto delivery devices. The method includes washing, with a sterile solution, a collapsible medical device that is stored within a tapered interior volume of a loading device in a partially collapsed state. The method also includes coupling a delivery device to a retainer positioned within the loading device. The retainer maintains the collapsible medical device within the loading device in the partially collapsed state prior to connection to the delivery device. Additionally, the method includes retracting the retainer through a loading channel of the loading device, where retracting retainer causes the collapsible medical device to move through the tapered interior volume to compress the collapsible medical device. The method includes removing the loading device from the delivery device. The method also includes sealing the collapsible medical device within the delivery device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

FIGS. 2A-2C depict several illustrations of a locking collar assembly of the loading system of FIGS. 1A and 1B, according to an embodiment hereof.

FIGS. 9A-9I depict several illustrations of the operation of the loading system of FIGS. 1A and 1B, according to an embodiment hereof.

FIGS. 17A-17I depict several illustrations of the operation of the loading system of FIGS. 10A and 10B, according to an embodiment hereof.

DETAILED DESCRIPTION

Specific embodiments of the present disclosure are now described with reference to the figures, wherein like reference numbers indicate identical or functionally similar elements.

The following detailed description describes examples of embodiments and is not intended to limit the present technology or the application and uses of the present technology. Although the description of embodiments hereof is in the context of a storage and loading device for a prosthetic heart valve, the present technology may also be used for other devices. Furthermore, there is no intention to be bound by any expressed or implied theory presented in the preceding technical field, background, brief summary or the following detailed description.

Embodiments of disclosed herein are directed to a loading system for storing an implantable medical device and loading the implantable medical device onto a delivery device. In embodiments, the loading system stores the medical device, e.g., a prosthetic heart valve, in a partially compressed or "loaded" state. The loading system stores the medical device in a preserving fluid to enable the medical device to be stored for a period of time without degrading the medical device. When the medical device is ready to be implanted, the loading system is attached to a delivery device. The loading system enables the medical device to be loaded in the delivery device without direct interaction with the medical device. As such, the loading system can provide for storing and loading implantable medical devices at a reduced cost and in a portable fashion. The integrated design of the loading system reduces the steps to clean, sterilize, and load the implantable medical device.

Figure 1A:
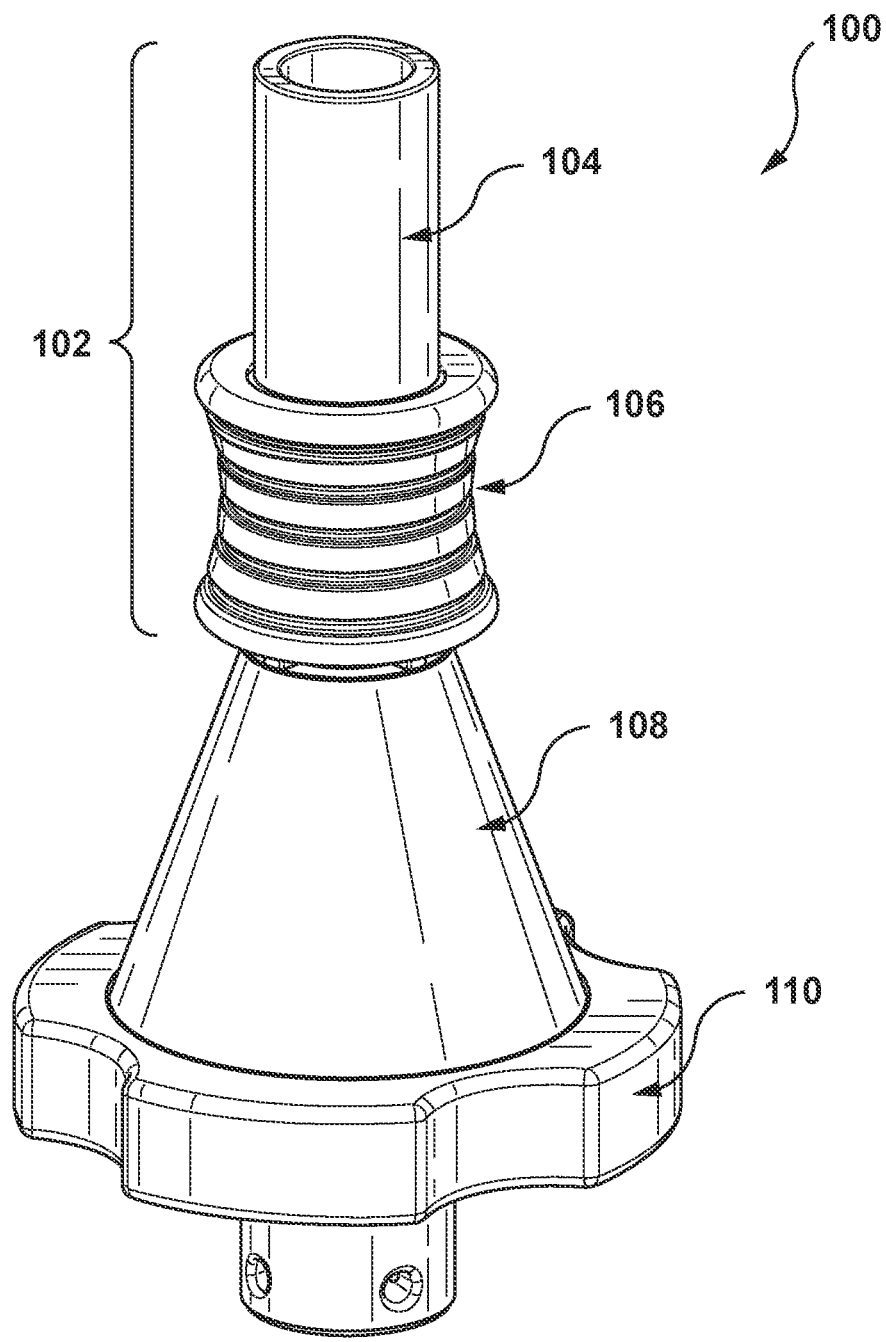
FIG. 1A depicts a perspective illustration of a loading system for use with a medical device, according to an embodiment hereof.
Figure 1B:
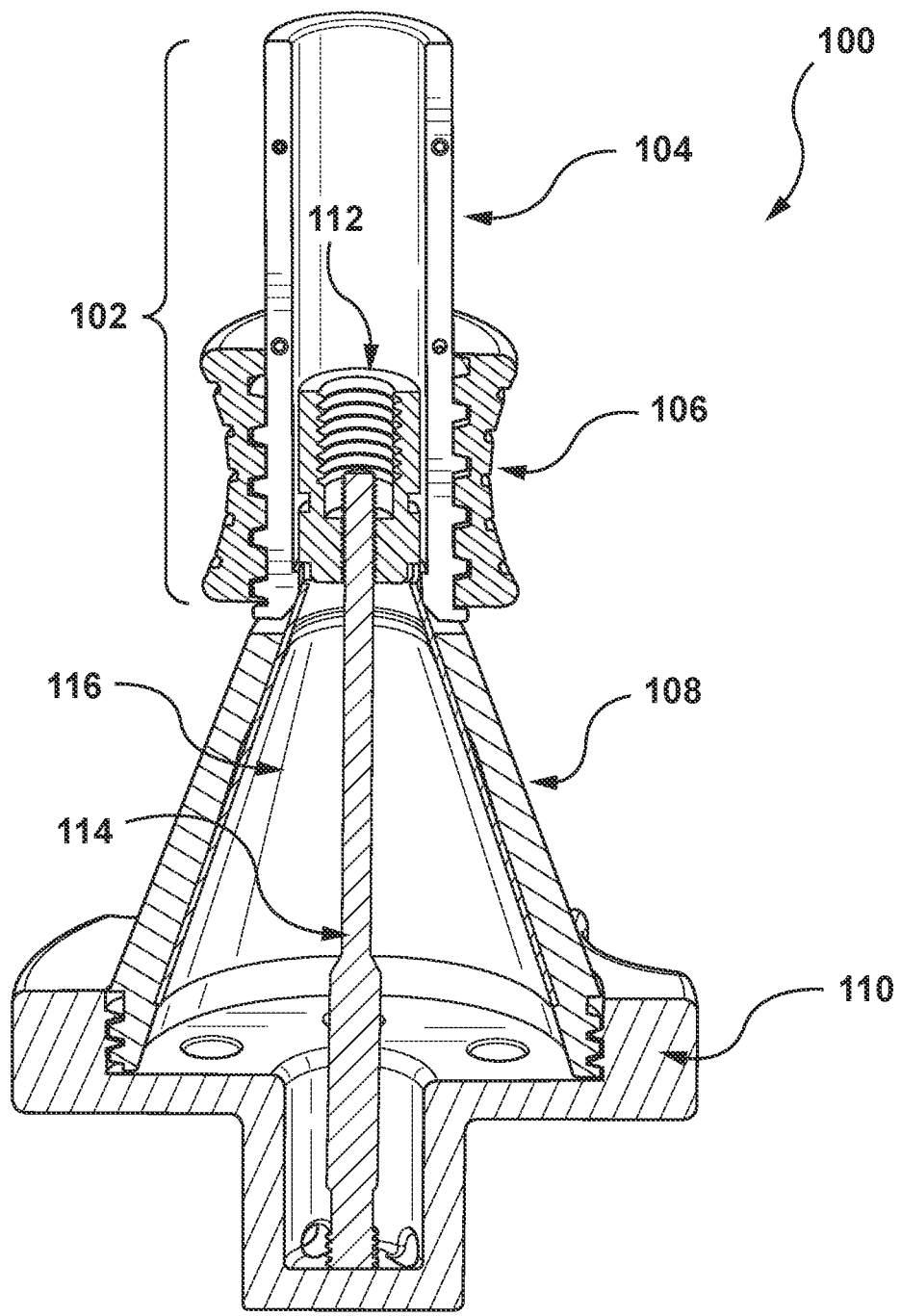
FIG. 1B depicts a cross-sectional illustration of the loading system of FIG. 1A, according to an embodiment hereof.

FIGS. 1A and 1B illustrate an example of a loading system 100 in accordance with an embodiment hereof. One skilled in the art will realize that FIGS. 1A and 1B illustrate one example of a loading system and that existing components illustrated in FIGS. 1A and 1B may be removed and/or additional components may be added to the loading system 100.

As illustrated in FIG. 1A, the loading system 100 includes a locking collar assembly 102, which includes a split collar 104 and a locking collar 106. The loading system 100 also includes a loading funnel 108 and a funnel cap 110. As illustrated in FIG. 1B, the locking collar assembly 102 includes a device retainer 112 and a nosecone pin 114. When coupled to the loading system 100, the device retainer 112 is positioned within the locking collar 106 of the locking collar assembly 102. The nosecone pin 114 is coupled to the device retainer 112 and extends through the loading funnel 108.

The device retainer 112 is coupled to an implantable medical device 116. In embodiments, any type of implantable medical device that requires a conversion from an uncompressed state to a compressed state and that requires loading onto a delivery device can be utilized with the loading system 100. In an embodiment, the implanted medical device 116 can include components that are intended to repair or support systems of the human body, e.g., prosthetic heart valves including organic tissue coupled to self-expandable or balloon-expandable stents/frames. For example, the loading system 100 can be utilized on implantable medical devices that are to be delivered transluminally, e.g., via a catheter, and need to be loaded onto or into a catheter. The stent/frame may be radially compressed to have a low profile and loaded into/onto a delivery device such that the heart valve prosthesis can be delivered through the vessels to a target location in a compressed state, and then expanded at the target location, by a self-expanding stent/frame or a balloon of the delivery device, for instance, to replace the native heart valve.

The loading system 100 is configured to store the implantable medical device 116 in a partially compressed or "loaded" state. That is, the loading funnel 108 is configured to apply a force to the implantable medical device 116 to partially compress the implantable medical device 116 and maintain the implantable medical device 116 in the partially compressed state during storage. In embodiments, as further described below, the loading funnel 108 is formed with a tapered interior chamber that maintains the implantable medical device 116 in a partially compressed state and operates to further compress the implantable medical device 116 when loading the implantable medical device 116 onto a delivery device.

The locking collar assembly 102 enables a delivery device, e.g., catheter, to be attached to device retainer 112 with minimal interaction with the implantable medical device 116. In an embodiment, as further described below, a delivery device (or component of the delivery device) is inserted into the locking collar assembly 102 and attached to the device retainer 112. To load the implantable medical device 116, the device retainer 112 is retracted into the delivery device. As the device retainer 112 is retracted, the implantable medical device 116 is further compressed by the loading funnel 108.

Figure 2A:
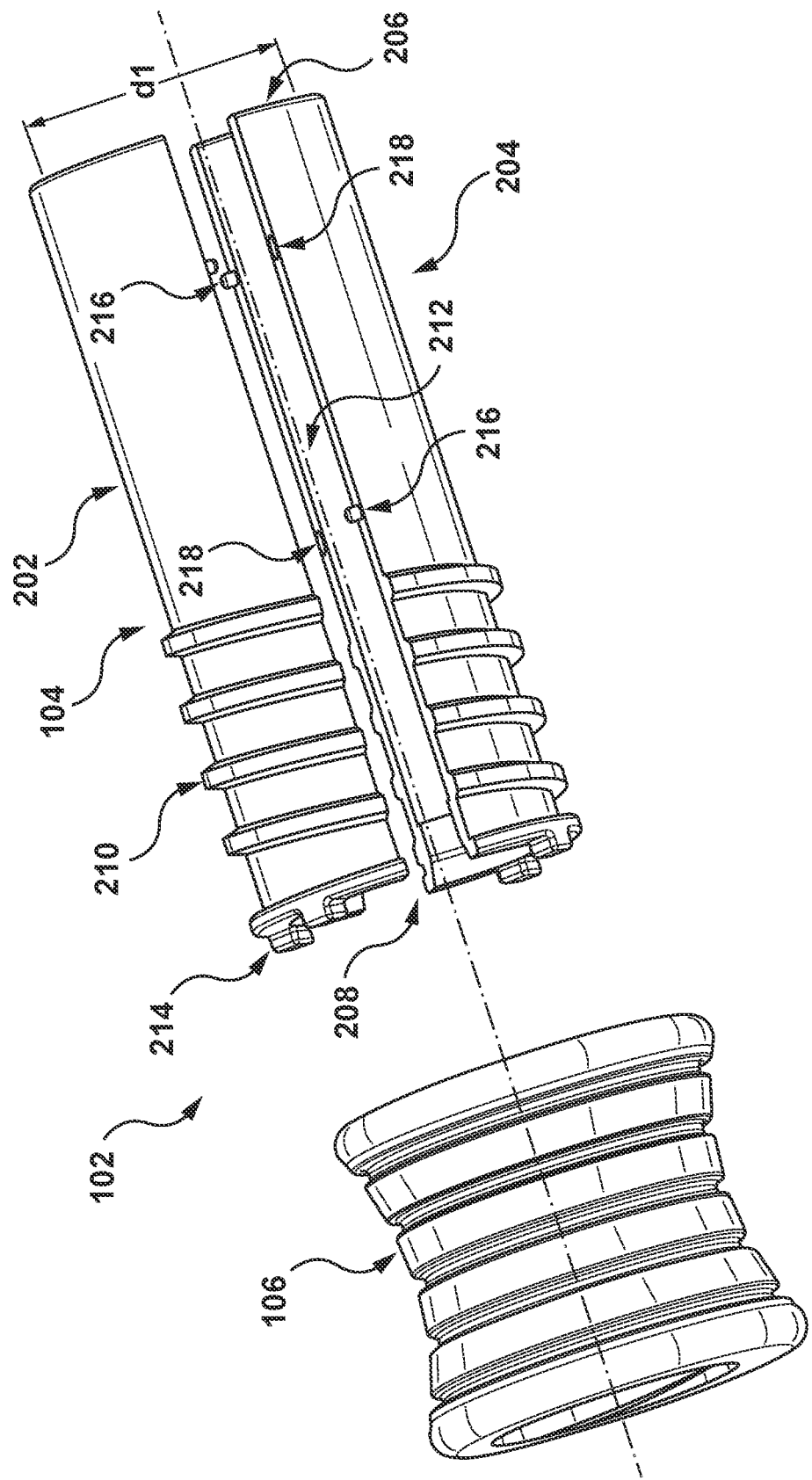
Figure 2B:
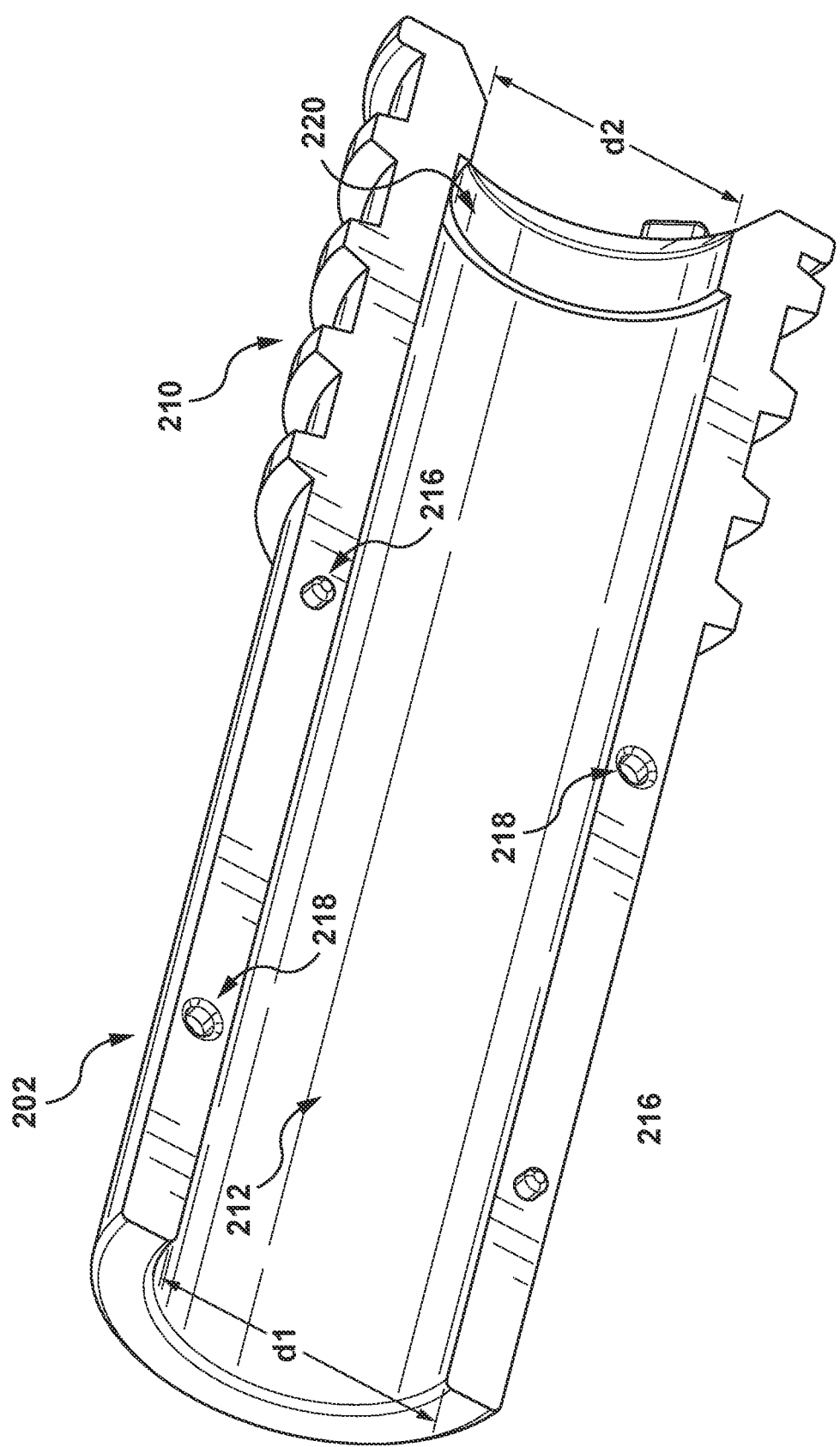

FIGS. 2A-2C illustrate an example of the locking collar assembly 102 in accordance with an embodiment hereof. One skilled in the art will realize that FIGS. 2A-2C illustrate one example of a locking collar assembly and that existing components illustrated in FIGS. 2A-2C may be removed and/or additional components may be added to the locking collar assembly 102.

As illustrated in FIG. 2A, the split collar 104 includes a first collar half 202 and a second collar half 204. The first collar half 202 and the second collar half 204, when joined, form a proximal opening 206, a distal opening 208, and a loading channel 212. The loading channel 212 is formed in an approximate cylindrical shape with circular cross-section having an inner diameter, $d_1$. The loading channel 212 is formed with the diameter, $d_1$, to accommodate the device retainer 112 and allow the insertion of a delivery device, e.g., a catheter, into the split collar 104. In embodiments, the diameter, $d_1$, of the loading channel 212 may depend on the French (FR) size of the catheter. For example, the diameter, $d_1$, of the loading channel 212 may be formed to accommodate a 18-33 Fr catheter. In an embodiment, the delivery device may be inserted into the proximal opening 206, and the device retainer 112 may be positioned at or near the distal opening 208. The split collar 104 can be formed of any suitable material such as, but not limited to a polymeric material.

For example, the loading system 100 may be configured to store and load a 42 millimeter (mm) transcatheter mitral valve replacement device (TMVR), e.g., heart valve and frame. In such as embodiment, the loading channel 212 may be formed with a diameter, $d_1$, in a range of approximately 6 mm to approximately 13 mm. In another example, the loading system 100 may be configured to store and load a 48 mm TMVR device. In such an embodiment, the loading channel 212 may be formed with a diameter, $d_1$, in a range of approximately 6 mm to approximately 13 mm. One skilled in the art will realize that the loading channel 212 can be formed to any dimension and/or cross-sectional shape to accommodate different medical devices and or delivery devices.

The first collar half 202 and the second collar half 204 include tabs 214. The tabs 214 can be configured to provide a connection and/or interface point to the loading funnel 108. The tabs 214 allow fluid to enter an interior space of the split collar 104 and allow air to exit interior space of the split collar 104. This may prevent air does from becoming trapped between the implantable medical device 116 and the delivery device.

The first collar half 202 and the second collar half 204 include connector pins 216 and connector holes 218. The connector pins 216 are aligned with the connector holes 218 to engage with the connector holes 218 when the first collar half 202 and the second collar half 204 are joined to form the split collar 104. The split collar 104 includes the first collar half 202 and the second collar half 204 to allow the spilt collar 104 to be separated and removed once the implantable medical device 116 is loaded into the delivery device.

As illustrated in FIG. 2B, the split collar 104 also includes a circular ridge 220 positioned adjacent to and/or near the distal opening 208. The circular ridge 220 extends radially inward from the inner surface of the split collar 104. In an embodiment, the circular ridge 220 can be formed in an approximate ring and/or torus shape. The circular ridge 220 is formed to a diameter, $d_2$, that is smaller than the diameter, $d_1$, of the loading channel 212. In an embodiment, the circular ridge 220 can be formed to a diameter, $d_2$, that is larger than the diameter of the device retainer 112, but smaller than the outer diameter of the delivery device, for example, an outer shaft of the delivery device, to be inserted into the locking collar 104. In this embodiment, the circular ridge 220 can function to prevent the implantable medical device 116 from contacting contact with the delivery device during loading, i.e., provides protection for the implantable medical device 116 during loading.

The split collar 104 includes male threads 210 are formed on an outer surface of the split collar 104 and are positioned at or near the distal opening 208. The male threads 210 are configured to engage female threads 256 (illustrated in FIG. 2C) of the locking collar 106 and secure the split collar 104 to the locking collar 106. The female threads 256 are formed on an inner surface of the locking collar 106 and are positioned along an entire length of the inner surface of the locking collar 106. As described herein, a "female" threads and/or connectors are generally receptacles that receive and hold "male" threads and/or connectors. Once the locking collar 106 is secured to the split collar 104, the locking collar 106 applies a force to the first collar half 202 and the second collar half 204 to hold the first collar half 202 and the second collar half 204 together.

While FIGS. 2A-2C illustrate threads for coupling the split collar 104 and the locking collar 106, one skilled in the art will realize that other types of connectors can be utilized to mechanically couple the split collar 104 and the locking collar 106. In some embodiments, the split collar 104 and the locking collar 106 can include a push fit locking collar that acts as an interference fit for coupling the split collar 104 and the locking collar 106. For example, an outer diameter of the split collar 104 may be larger than an inner diameter of the locking collar 106. In some embodiments, the split collar 104 and the locking collar 106 can include a c-clip mechanism connector that acts as a mechanical interference between the split collar 104 and the locking collar 106. In some embodiments, the split collar 104 and the locking collar 106 can include a snap fit connection (e.g., cantilever, torsional and/or annular). For example, the split collar 104 can include a protruding edge or tab, and the locking collar 106 can include a snap-in area (e.g., groove, channel, etc.) for receiving and locking the protruding edge or tab. Likewise, for example, the locking collar 106 can include a protruding edge or tab, and the split collar 104 can include a snap-in area (e.g., groove, channel, etc.) for receiving and locking the protruding edge or tab.

As illustrated in FIGS. 2A and 2C, the locking collar 106 includes a first end 250 and a second end 252. The locking collar 106 includes external ridges 254. The external ridges 254 can provide a textured surface to assist in the securing of the locking collar 106 to the split collar 104. The locking collar 106 can be formed of any suitable material such as, but not limited to a polymeric material.

Figure 3A:
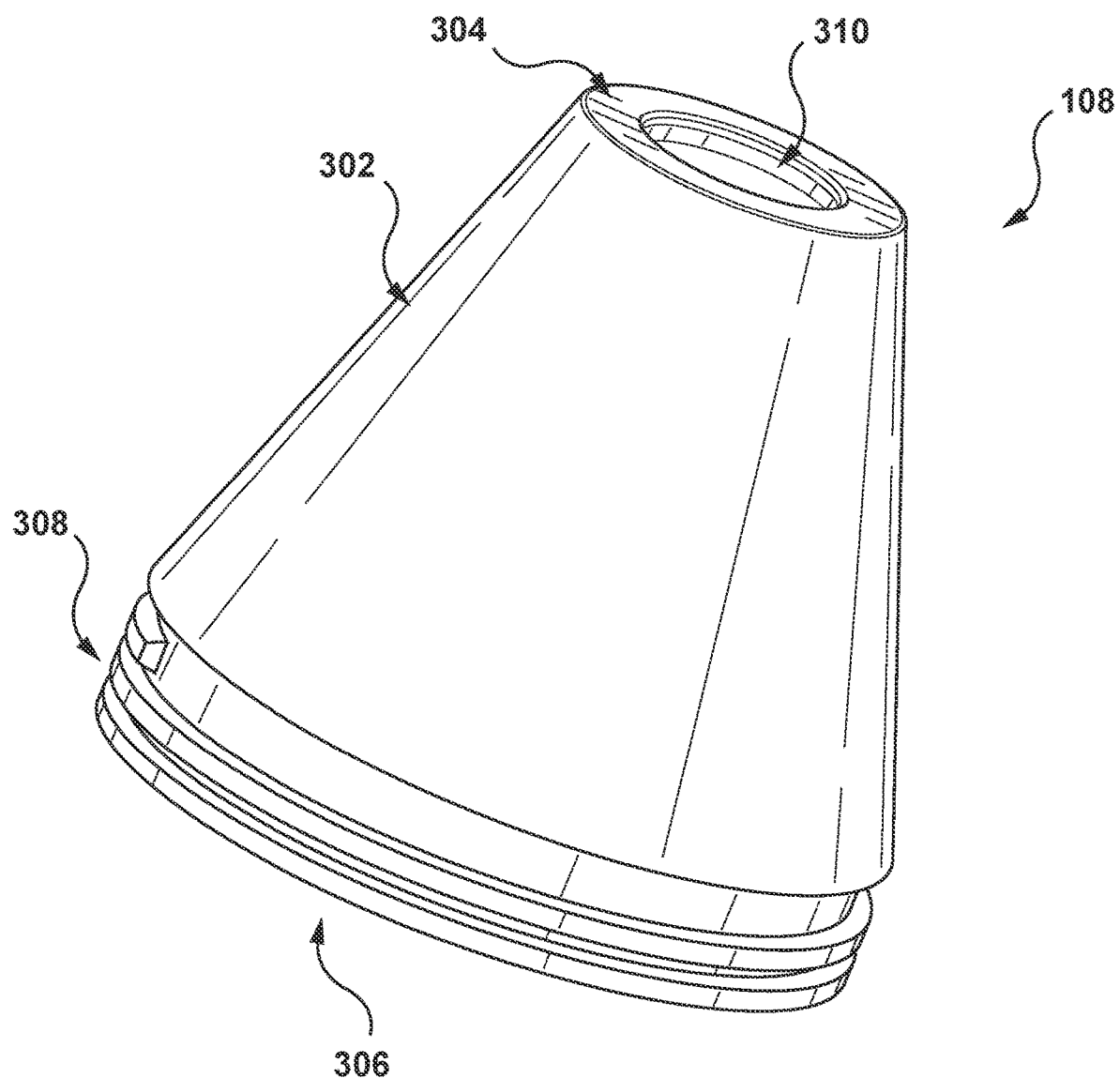
FIGS. 3A and 3B depict illustrations of a loading funnel of the loading system of FIGS. 1A and 1B, according to an embodiment hereof.
Figure 3B:
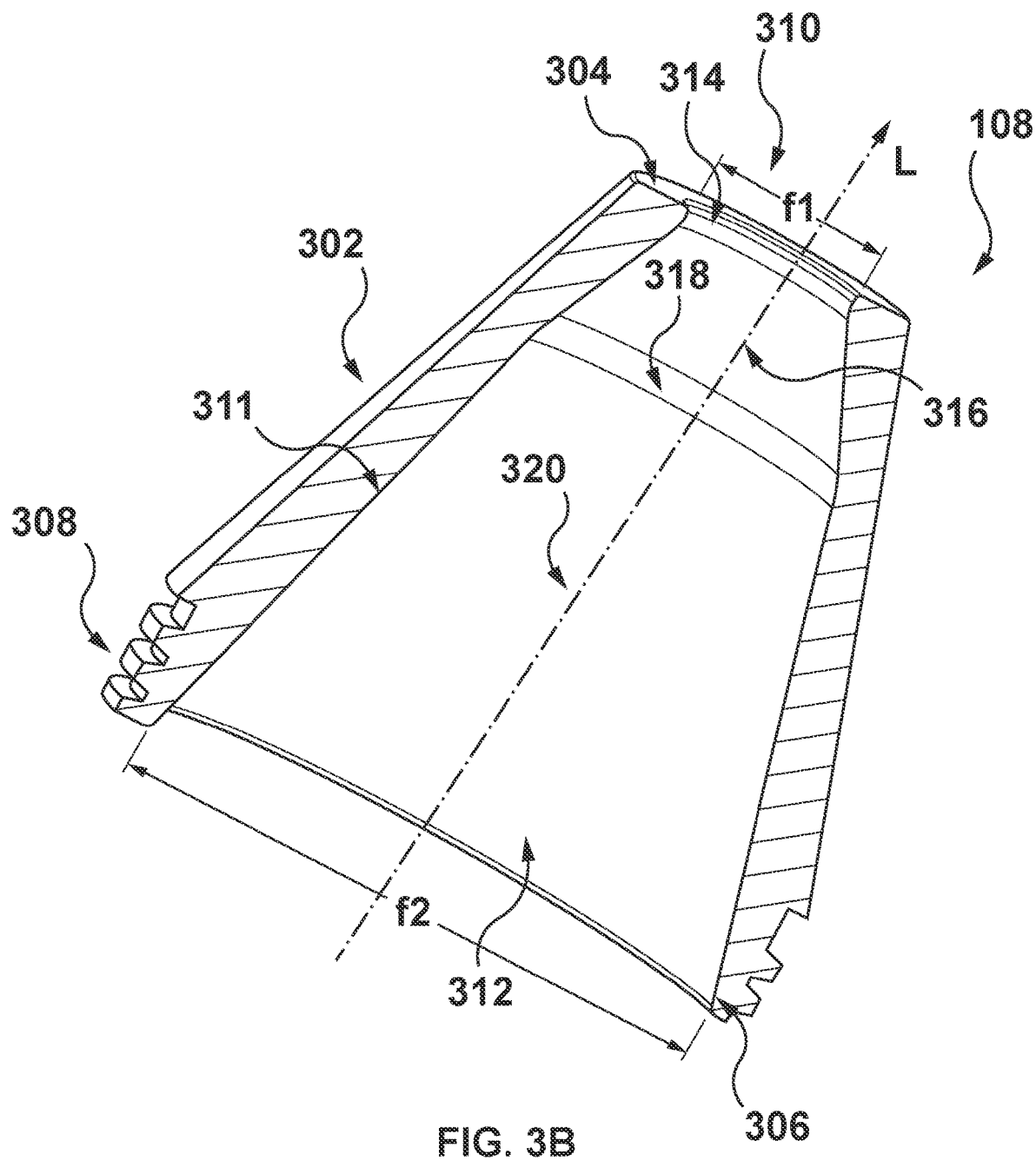

FIGS. 3A and 3B illustrate an example of the loading funnel 108 in accordance with an embodiment hereof. One skilled in the art will realize that FIGS. 3A and 3B illustrate one example of a loading funnel and that existing components illustrated in FIGS. 3A and 3B may be removed and/or additional components may be added to the loading funnel 108.

As illustrated in FIG. 3A, the loading funnel 108 includes a funnel body 302 with a proximal end 304 and a distal end 306. The funnel body 302 is formed in an approximate conical shape with the proximal end 304 having a smaller diameter than the distal end 306. The loading funnel 108 includes male threads 308 formed on an outer surface of the loading funnel at the distal end 306 of the funnel body 302. The male threads 308 are configured to engage with female threads of the funnel cap 110, described below. The funnel body 302 can be formed on any suitable material such as, but not limited to stainless steel.

As illustrated in FIGS. 3A and 3B, the loading funnel 108 includes a proximal opening 310 formed in the proximal end 304 of the funnel body 302 having a diameter, $f_1$. The loading funnel 108 also includes a distal opening 312 formed in the distal end 306 of the funnel body 302 having a diameter, $f_2$. The interior of the funnel body 302 forms a compression volume 311. The compression volume 311 is formed in an approximate funnel or cone shape with a decreasing volume from the distal end 306 to the proximal end 304 of the funnel body. In an embodiment, the compression volume 311 is tapered, in a decreasing diameter, from diameter, $f_2$, at the distal end 306 to the diameter, $f_1$, at the proximal end 304. The compression volume 311 can be formed of a first funnel section 314, a second funnel section 316, a third funnel section 318, and a fourth funnel section 320. Each of the first funnel section 314, the second funnel section 316, the third funnel section 318, and the fourth funnel section 320 can be formed in the shape of a funnel, each with a different degree of decreasing volume from the distal end 306 to the proximal end 304. In embodiments, the volume of the compression volume 311 operates to maintain the implantable medical device 116 in a partially compressed state during storage.

In embodiments, the degree of decreasing volume, e.g., taper angle, can affect the angle at which the implant attachment tabs exit the funnel, with a longer taper improving the loading of the implantable medical device 116. The longer taper may provide a smoother transition for the implantable medical device 116 during loading into the delivery device. A short taper may apply compressive strain on the implantable medical device 116, may require high force during loading, may result in an uneven crimp, may cause inflooding of the implantable medical device 116, or may apply an additional compressive load on the implantable medical device 116 when stored. According the degree of decreasing volume, e.g., taper angle, may be set to minimize these and ensure integrity of the implantable medical device 116.

In embodiments, the decreasing volume of the compression volume 311 operates to apply a compression force on the implantable medical device 116 as device retainer 112 is retracted through the loading channel 212. That is, as the device retainer 112 is retracted into the delivery device positioned in the loading channel 212, the implantable medical device 116 retracts in a loading direction, L, through the proximal opening 310. As the implantable medical device 116 moves through the compression volume 311, the inner surfaces of the loading funnel body 302 apply a compression force on surfaces of the implantable medical device 116.

In embodiments, the diameter, $f_1$, of the proximal opening 310 may depend on the FR size of the catheter. For example, the diameter, $f_1$, of the proximal opening 310 may be formed to accommodate a 18-33 Fr catheter. In embodiments, the diameter, $f_2$, of the distal opening 312 may depend on an outer diameter of the implantable medical device 116.

In some embodiments, the loading system 100 may be configured to store and load a 42 mm TMVR device, and In such an embodiment, the diameter, $f_1$, can be in a range of approximately 6 mm to approximately 13 mm, and the diameter, $f_2$, can be in the range of approximately 20 mm to approximately 60 mm. In another example, the loading system 100 may be configured to store and load a 48 mm TMVR device, and the proximal opening 310 may be formed with a diameter, $f_1$, and the distal opening 312 may be formed with a diameter, $f_2$. In such an embodiment, the diameter, $f_1$, can be in a range of approximately 6 mm to approximately 13 mm, and the diameter, $f_2$, can be in the range of approximately 20 mm to approximately 60 mm. One skilled in the art will realize that the compression volume 311 can be formed to any dimension and/or cross-sectional shape to accommodate different medical devices and or delivery devices.

Figure 4A:
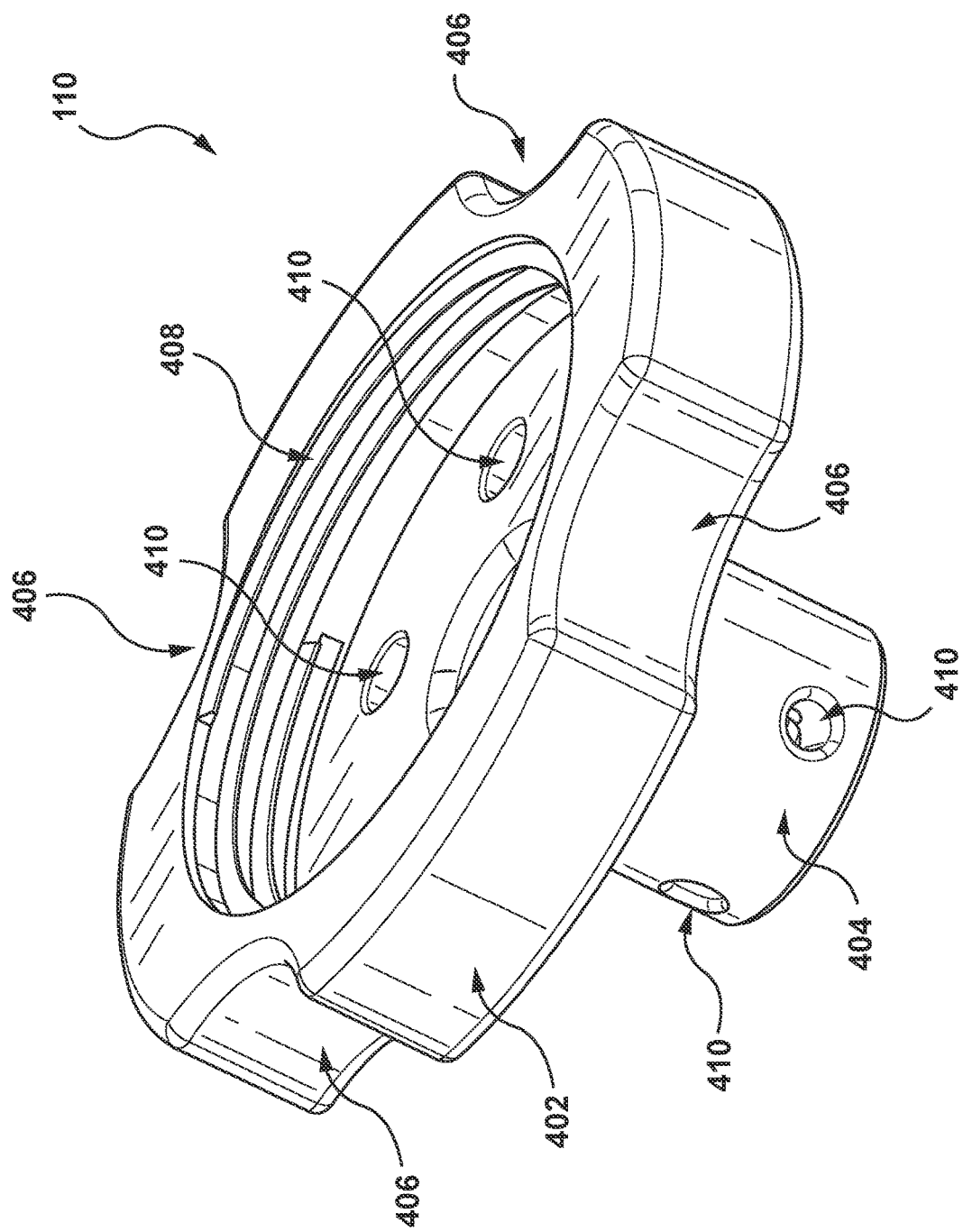
FIGS. 4A and 4B depict illustrations of a funnel cap of the loading system of FIGS. 1A and 1B, according to an embodiment hereof.
Figure 4B:
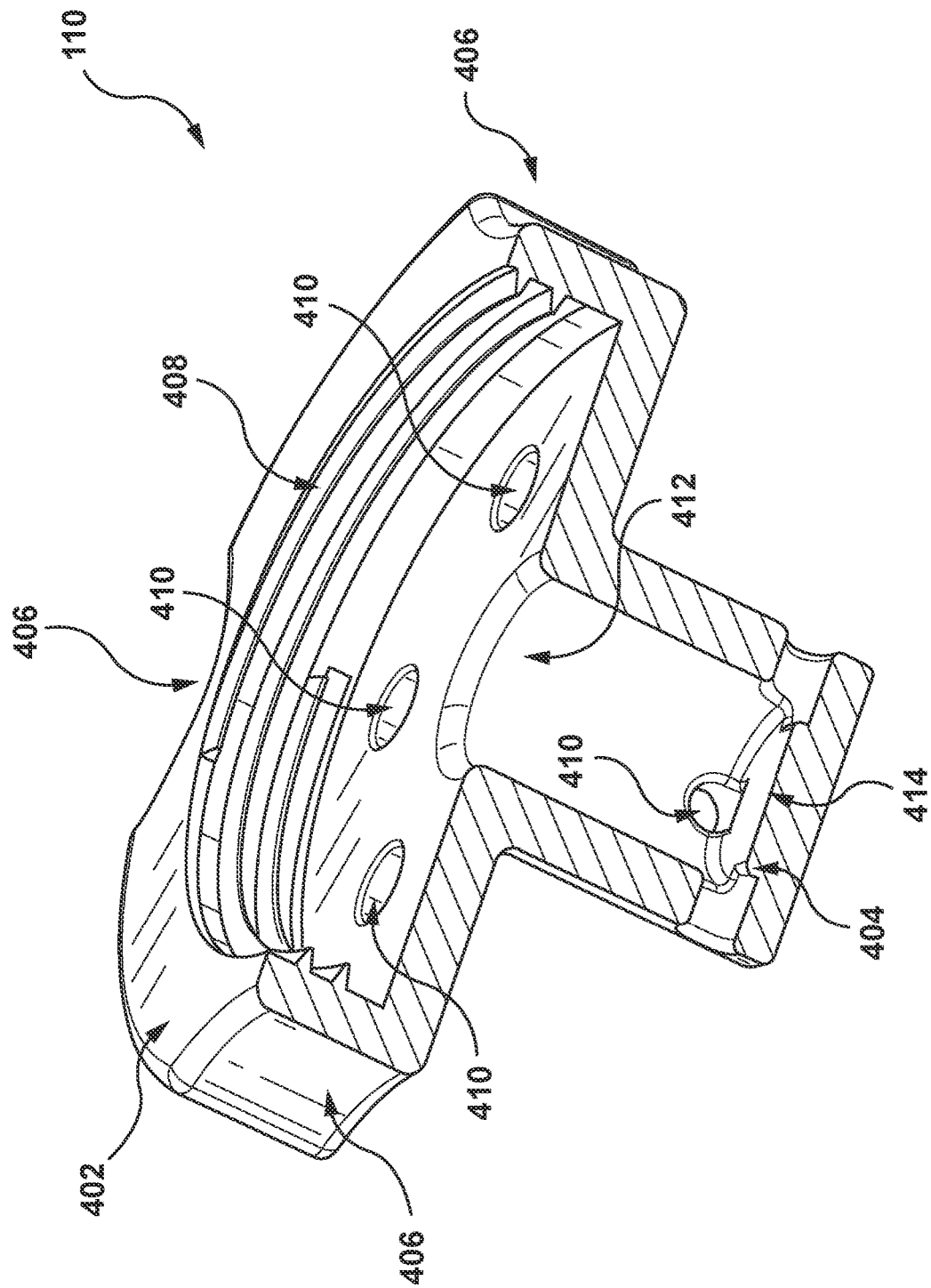

FIGS. 4A and 4B illustrate an example of the funnel cap 110 in accordance with an embodiment hereof. One skilled in the art will realize that FIGS. 4A and 4B illustrate one example of a funnel cap and that existing components illustrated in FIGS. 4A and 4B may be removed and/or additional components may be added to the funnel cap 110.

As illustrated in FIG. 4A, the funnel cap 110 includes a cap body 402 and a nosecone pin housing 404. The cap body 402 can be formed in an approximate cylindrical shape and includes cap indentations 406. For example, as illustrated in FIG. 4A, the cap body 402 can include four (4) cap indentations 406 positioned at opposing location around the cap body 402. The cap indentations 406 can provide a location to apply leverage when removing the funnel cap 110 from the loading funnel 108, as described below in further detail. The cap body 402 can be formed of any suitable material such as, but not limited to a polymeric material.

The cap body 402 can also include female threads 408 formed on an interior surface of the cap body 402. The female threads 408 can be formed to match and engage with the male threads 308 of the exterior surface of the loading funnel 108 to secure the funnel cap 110 to the loading funnel 108. The nosecone pin housing 404 can be formed in an approximate cylindrical shape. The nosecone pin housing 404 is configured to hold the nosecone pin 114. That is, when the nosecone pin 114 is stored within the loading system 100, the nosecone pin 114 abuts a bottom surface of the nosecone pin housing 404. The sidewalls of the nosecone pin housing 404 hold the nosecone pin 114 in position and prevent the nosecone pin 114 from moving laterally within the loading system 100. The nosecone pin housing 404 can be formed of any suitable material such as, but not limited to a polymeric material.

As illustrated in FIGS. 4A and 4B, the cap body 402 and the nosecone pin housing 404 includes port 410. The ports 410 can be configured to enable fluid to enter and exit the interior of the funnel cap 110. The funnel cap 110 operates to prevent the device retainer 112 and the implantable medical device 116 from exiting the distal opening 312 of the loading funnel 108. That is, the nosecone pin housing 404 (e.g., bottom surface) applies a force on the nosecone pin 114, which is attached to the device retainer 112, to prevent the device retainer 112 and the implantable medical device 116 from sliding distally out of the loading funnel 108 due to compression force of the loading funnel 108 when the implantable medical device 116 is in a partially compressed state.

While FIGS. 3A, 3B, 4A and 4B illustrate threads for coupling the loading funnel 108 and the funnel cap 110, one skilled in the art will realize that other types of connectors can be utilized to mechanically couple the loading funnel 108 and the funnel cap 110. In some embodiments, the loading funnel 108 and the funnel cap 110 can include a push fit locking collar that acts as an interference fit for coupling the loading funnel 108 and the funnel cap 110. For example, an outer diameter of the loading funnel 108 may be larger than an inner diameter of the funnel cap 110. In some embodiments, the loading funnel 108 and the funnel cap 110 can include a c-clip mechanism connector that acts as a mechanical interference between the loading funnel 108 and the funnel cap 110. In some embodiments, the loading funnel 108 and the funnel cap 110 can include a snap fit connection (e.g., cantilever, torsional and/or annular). For example, the loading funnel 108 can include a protruding edge or tab, and the funnel cap 110 can include a snap-in area (e.g., groove, channel, etc.) for receiving and locking the protruding edge or tab. Likewise, for example, the funnel cap 110 can include a protruding edge or tab, and the loading funnel 108 can include a snap-in area (e.g., groove, channel, etc.) for receiving and locking the protruding edge or tab.

Figure 5A:
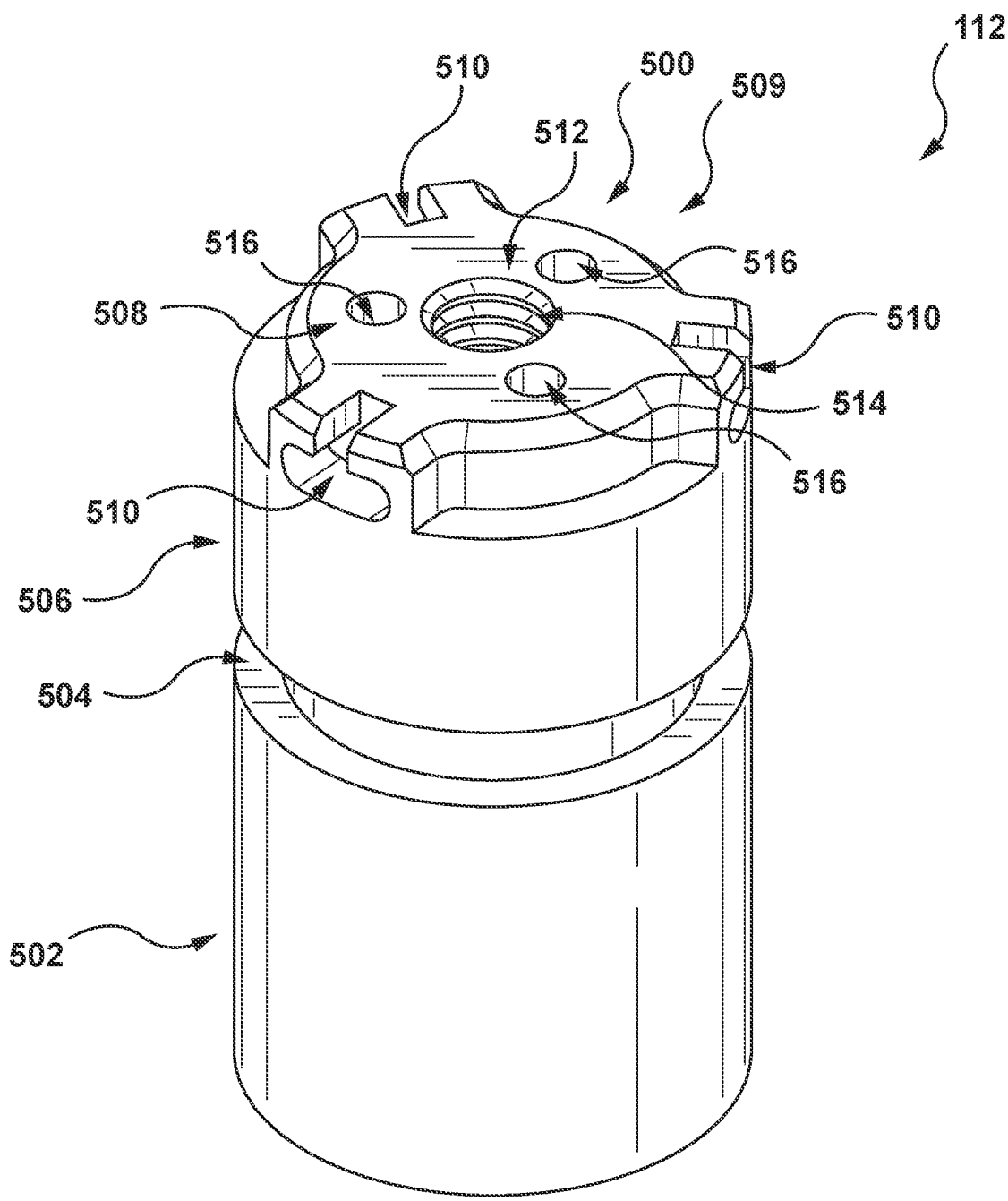
FIGS. 5A and 5B depict illustrations of a device retainer of the loading system of FIGS. 1A and 1B, according to an embodiment hereof.
Figure 5B:
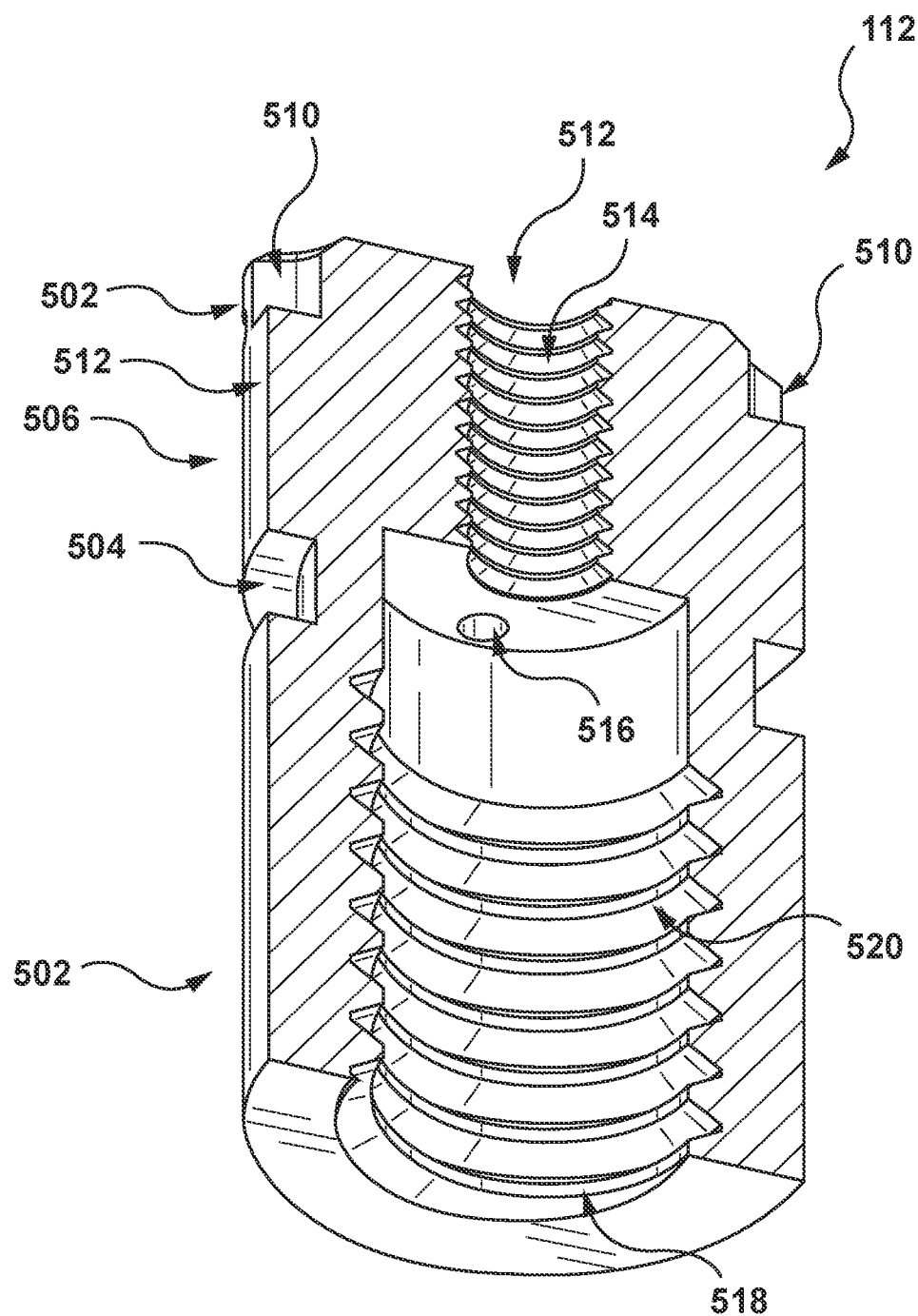

FIGS. 5A and 5B illustrate an example of the device retainer 112 in accordance with an embodiment hereof. One skilled in the art will realize that FIGS. 5A and 5B illustrate one example of a device retainer and that existing components illustrated in FIGS. 5A and 5B may be removed and/or additional components may be added to the device retainer 112.

As illustrated in FIG. 5A, the device retainer 112 includes a first section 502 formed at a proximal end of the device retainer 112 and a third section 506 formed at a distal end 509 of the device retainer 112. The device retainer 112 also includes a second section 504 formed between the first section 502 and the third section 506. The first section 502 is configured to be coupled to the delivery device, as described in further detail below. The third section 506 is configured to be coupled to the implantable medical device 116. The first section 502, the second section 504, and the third section 506 are formed in a cylindrical shape. The second section 504 can be formed to an external diameter that is smaller than the first second 502 and the third section 506. In an embodiment, the second section 504 can operate as a channel to receive a sealing ring (e.g., o-ring). The sealing ring can operate to form hydraulic circuit in the delivery device as part of a pressurized system which closes components of the delivery device (e.g., capsule).

The device retainer 112 includes a fourth section 508 formed at the distal end 509 of the device retainer 112. The fourth section 508 includes locking channels 510, a distal opening 512, female threads 514, and ports 516. The locking channels 510 are configured to engage with the implantable medical device 116. In an example, the locking channels 510 may be T-shaped slots that are configured to receive T-shaped tabs on the frame/stent of the implantable medical device 116. That is, T-shaped tabs on the implantable medical device 116 may be configured to lock into the T-shaped slots of the locking channels 510 to secure the implantable medical device 116 to the device retainer 112. The ports 516 allow an operator of the delivery device de-gas regions around the implantable medical device 116 before and/or after the implantable medical device 116 is loaded. For example, liquid may be injected into a port in a proximal end at the delivery device and exits thru ports 516.

The female threads 514 are formed on inner surfaces of the third section 506 and the fourth section 508. The female threads 520 are configured to engage with male threads (e.g., male threads 616 as illustrated in FIG. 6) of the nosecone pin 114 to secure the nosecone pin 114 to the device retainer 112.

The device retainer 112 can be formed of any suitable material such as, but not limited to a polymeric material.

As illustrated in FIG. 5B, the device retainer 112 includes a proximal opening 518. The device retainer 112 includes female threads 520 from on an inner surface of the first section 502. The female threads 520 are configured to engage with male threads of the delivery device to secure the device retainer 112 to the delivery device.

Figure 6:
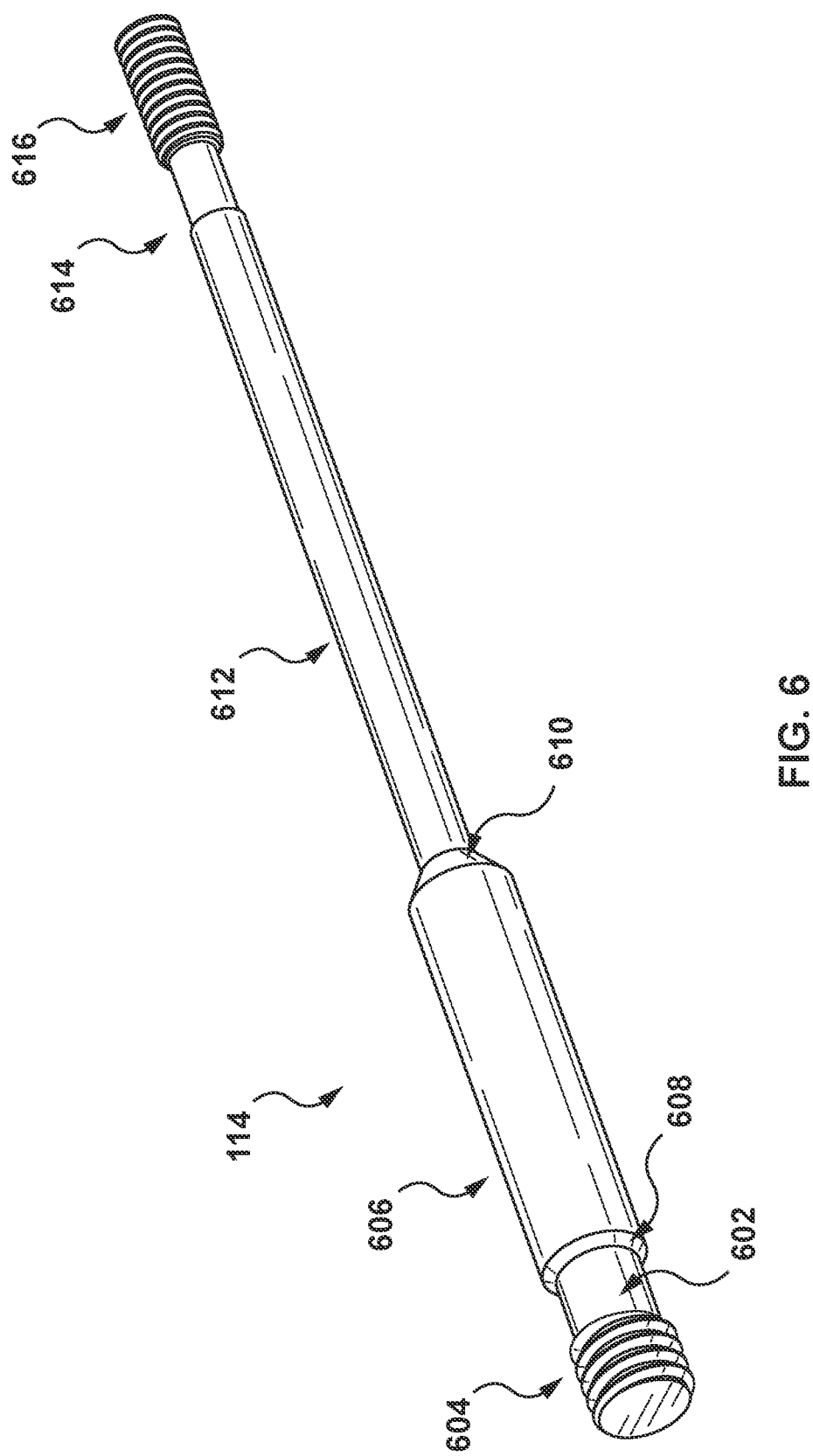
FIG. 6 depicts an illustration of a nosecone pin of the loading system of FIGS. 1A and 1B, according to an embodiment hereof.

FIG. 6 illustrates an example of the nosecone pin 114 in accordance with an embodiment hereof. One skilled in the art will realize that FIG. 6 illustrates one example of a nosecone pin and that existing components illustrated in FIG. 6 may be removed and/or additional components may be added to the nosecone pin 114.

As illustrated in FIG. 6, the nosecone pin 114 includes a first section 602 formed at a distal end of the nosecone pin 114. The first section 602 includes male threads 604 formed adjacent to and/or near the distal end of the nosecone pin 114. The male threads 604 are configured to engage with female threads of one or more devices that may be associated with the delivery device. For example, the male threads 604 can be configured to engage with female threads of a nosecone or cap that seals the delivery device once the implantable medical device 116 is loaded. The nosecone pin 114 can be formed of any suitable material such as, but not limited to a polymeric material.

The nosecone pin 114 includes a second section 606 that is formed adjacent to the first section 602. The second section 606 is formed in a cylindrical shape and includes a distal tapered edge 608 and a proximal tapered edge 610. The second section 606 is formed to a diameter that matches the delivery device, e.g., an outer shaft. The nosecone pin 114 includes a third section 612 formed adjacent to the second section 606 and a fourth section 614 formed adjacent to the third section 612. The third section 606 and the fourth section 614 are formed in a cylindrical shape. The fourth section 614 includes male threads 616 formed at a distal end of the nosecone pin 114. The male threads 616 are configured to engage with the female threads 512 of the device retainer 112.

Figure 7:
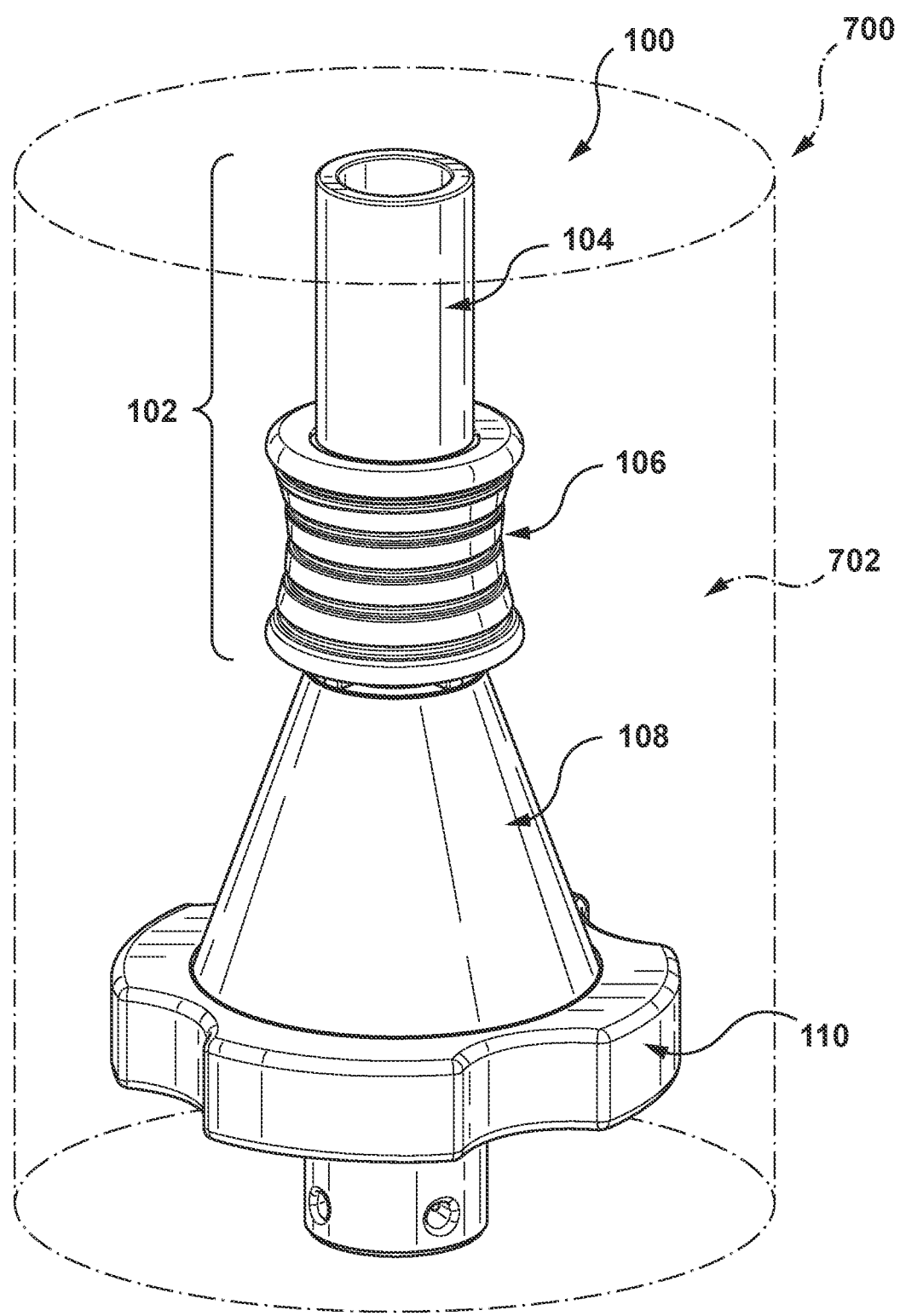
FIG. 7 depicts an illustration of a storage of the loading system of FIGS. 1A and 1B, according to an embodiment hereof.
Figure 8:
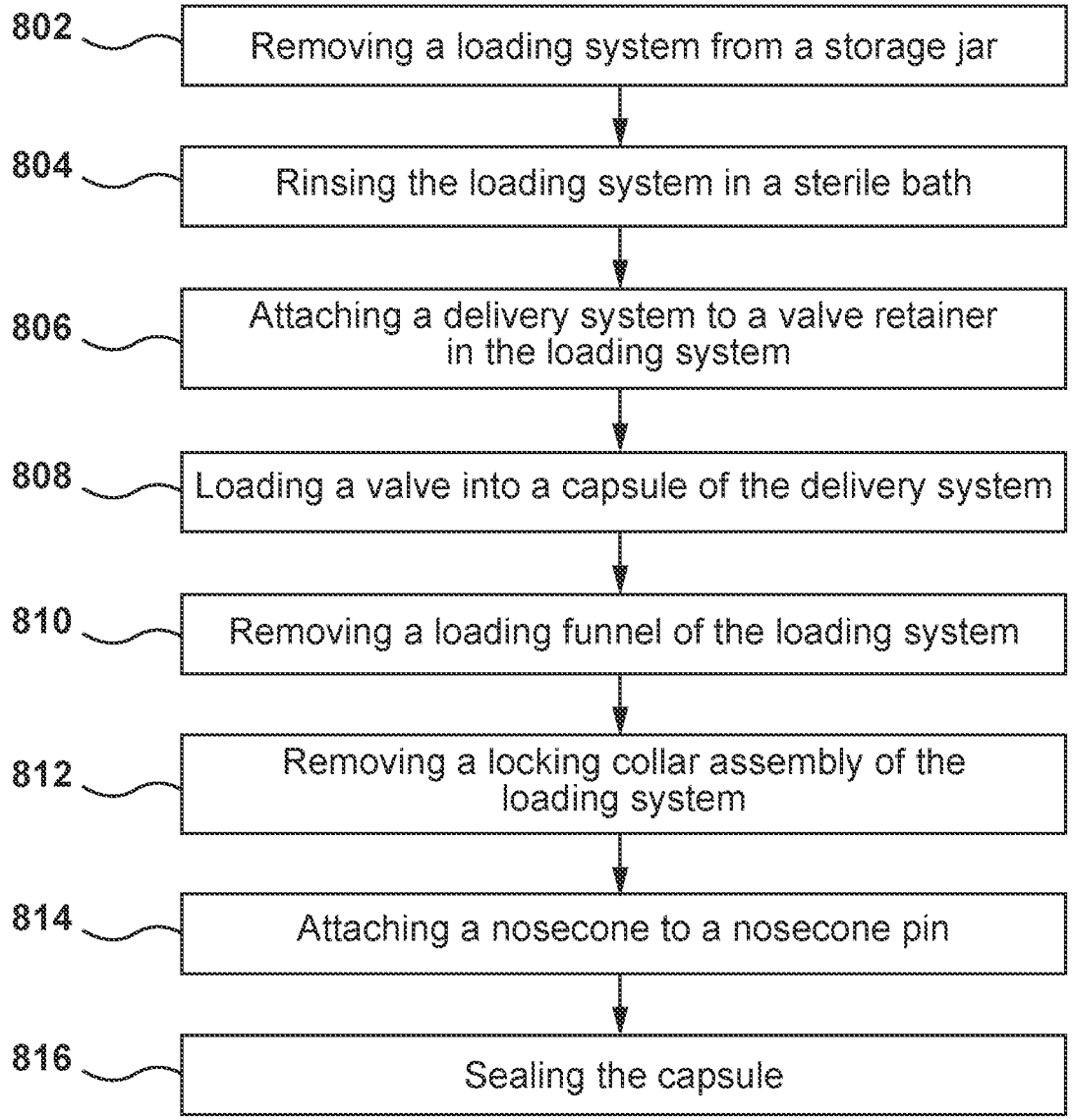
FIG. 8 depicts a flowchart of a process for the operation of the loading system of FIGS. 1A and 1B, according to an embodiment hereof.

FIG. 7 illustrates an example of a storage jar 700 in accordance with an embodiment hereof. One skilled in the art will realize that FIG. 7 illustrates one example of a storage jar and that existing components illustrated in FIG. 7 may be removed and/or additional components may be added to the storage jar 700.

In embodiments, the implantable medical device 116 can be loaded into the loading system 100. For example, the implantable medical device 116 can be coupled to the device retainer 112, and the nosecone pin 114 can be secured to the device retainer 112 by engaging the male threads 616 of the nosecone pin 114 and the female threads 514 of the device retainer 112. The device retainer 112 including the implantable medical device 116 and the nosecone pin 114 can be inserted into the loading funnel 108 and locking collar assembly 102 (attached to the loading funnel 108) to partially compress the implantable medical device 116. For example, the device retainer 112 can be inserted into the distal opening 306 of the loading funnel 108 and retracted through the loading funnel 108 into the loading channel 212 of the split collar 104. The funnel cap 110 can then be coupled to the loading funnel 108 by engaging the female threads 408 of the funnel cap 110 with the male threads 308 of the loading funnel 108.

Once the implantable medical device 116 is loaded into the loading system 100, the loading system 100 may be stored for a period of time until the implantable medical device 116 is utilized in a procedure. As such, the loading system 100 can be placed in the storage jar 700. The storage jar 700 can be filled with a preserving fluid 702. The preserving fluid 702 can be any type of fluid that maintains the integrity and quality of the loading system 100. For example, if the implantable medical device 116 include organic material, the preserving fluid 702 may include formaldehyde to maintain the integrity of the organic material.

FIG. 8 and FIGS. 9A-9I illustrate an example of a process 800 for the operation of the loading system 100 of FIGS. 1A and 1B to load the implantable medical device into a delivery device. While FIG. Band FIGS. 9A-9I illustrate various operations that can be performed in the process 800, one skilled in the art will realize that existing operations can be removed and additional operations can be added. Likewise, one skilled in the art will realize that the order of the operations can be changed in some instances.

In step 802, the process 800 includes removing a loading system from a storage jar. For example, the loading system 100 may be stored in the storage jar 700. The storage jar 700 can be unsealed and the loading system 100 removed, for example as illustrated in FIG. 9A.

In step 804, the process 800 includes rinsing the loading system in a sterile bath. For example, as illustrated in FIG. 9B, the loading system 100 with the implantable medical device 116 loaded therein can be placed in a sterile bath 902. The sterile bath 902 can include any suitable fluid, e.g., saline, to sterilize the loading system 100 and remove unwanted materials from the loading system 100. For example, the sterile bath 902 can be utilized to remove any preserving fluid 702 from the storage jar 700. When the loading system 100 is placed in the sterile bath 902 and agitated, the fluid of the sterile bath 902 wash the exterior of the loading system 100. Likewise, the fluid of the sterile bath 902 can enter the interior of the loading system 100, for example, through the ports 410, to wash the interior of the loading system 100 and the implantable medical device 116.

In step 806, the process 800 includes attaching a delivery device to a device retainer of the loading system. For example, as illustrated in FIG. 9C, a delivery device 904 can be attached to the device retainer 112. The delivery device 904 can include an outer shaft and an inner shaft that is disposed within a lumen of the outer shaft. The inner shaft can include male threads located at a distal end thereof that engage with the female threads 514 of the device retainer 112. The outer shaft can be inserted into the split collar 104 of the locking collar assembly 102. The inner shaft can be extended from the outer shaft and can be attached the device retainer 112, e.g., screwed into.

In step 808, the process 800 includes loading a valve into a capsule of the delivery device. In embodiments, the capsule can be the distal portion of the outer shaft of the delivery device 904. As illustrated in FIGS. 9D and 9E, the inner shaft can be retracted into the outer shaft. As the inner shaft is retracted, the device retainer 112 is also retracted into the outer shaft. Simultaneously, the implantable medical device 116 attached to the device retainer 112 is retracted in the loading direction, L, through the loading funnel 108. As the implantable medical device 116 moves through the compression volume 311, the inner surfaces of the loading funnel body 302 apply a compression force on surfaces of the implantable medical device 116.

In step 810, the process 800 includes removing a loading funnel of the loading system. As illustrated in FIG. 9F, the loading funnel 108 can be removed from the locking collar assembly 102. For example, the loading funnel 108 can be disengaged from the locking collar assembly 102. The partially compressed implantable medical device 116 exerts an outwards spring force on the loading funnel 108, which pulls the loading funnel 108 up against the locking collar assembly 102. This force may increase during loading until the locking collar assembly 102 exits the loading funnel 108 thereby releasing the loading funnel 108 from locking collar assembly 102.

In step 812, the process 800 includes removing a locking collar assembly of the loading system. As illustrated in FIG. 9G, the locking collar assembly 102 can be removed from the delivery device 904 in a single action. For example, the locking collar assembly 102 can be slid off the outer shaft of the delivery device 904. Likewise, in another example, the locking collar 106 can be removed from the split collar 104, and then the split collar 104 can be removed. For example, the split collar 104 can be disengaged, e.g., unscrewed, from the locking collar 106, and the split collar 104 can be separated into the first collar half 202 and the second collar half 204.

In step 814, the process 800 includes attaching a nosecone to a nosecone pin. For example, as illustrated in FIG. 9H, a nosecone 906 can be attached to the nosecone pin 114, for example, by engaging the male threads 604 with female threads of the nosecone 906.

In step 816, the process 800 includes sealing the capsule. For example, as illustrated in FIG. 9I, the inner shaft can be further retracted into the outer shaft until the nosecone 906 engages and creates a seal with the outer shaft.

Figure 10A:
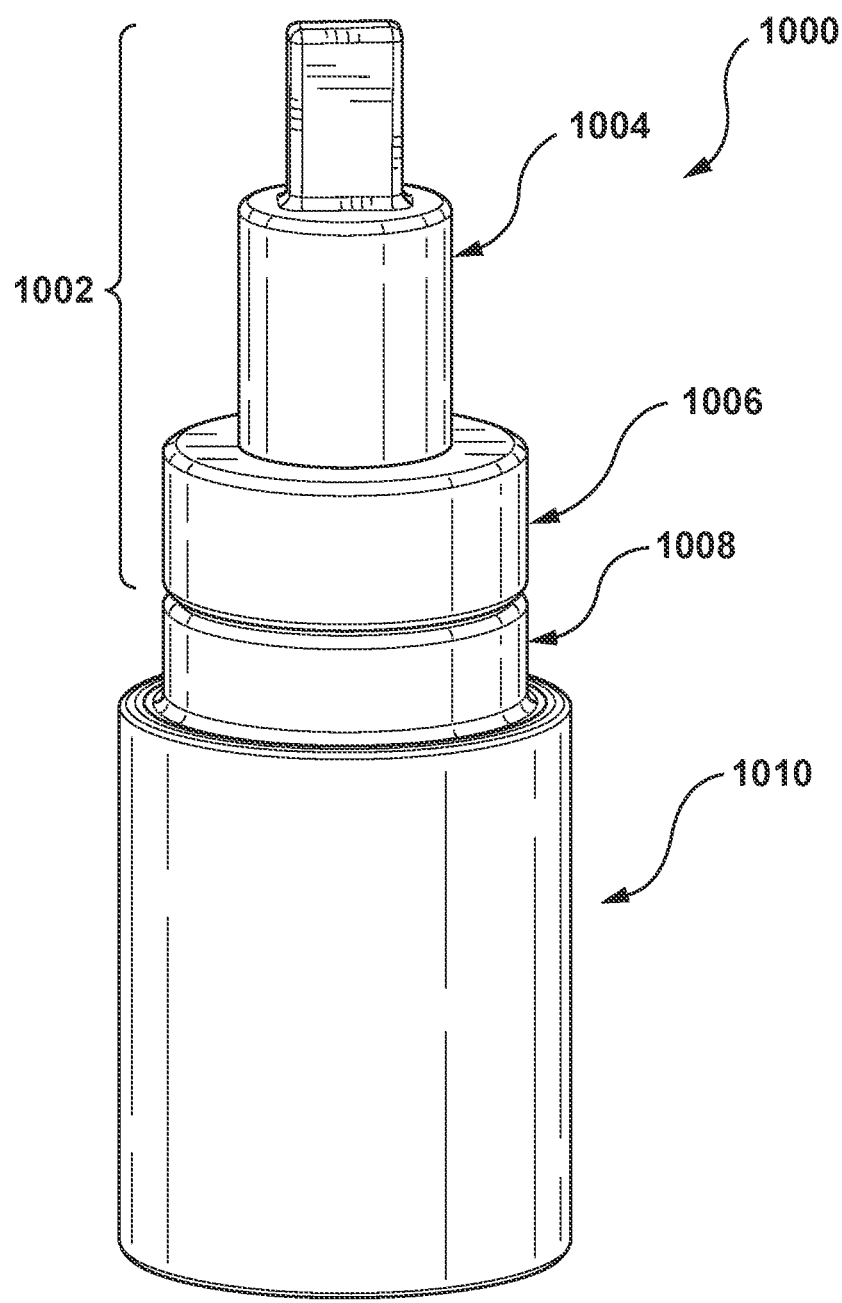
FIG. 10A depicts a perspective illustration of another loading system for use with a medical device, according to an embodiment hereof.
Figure 10B:
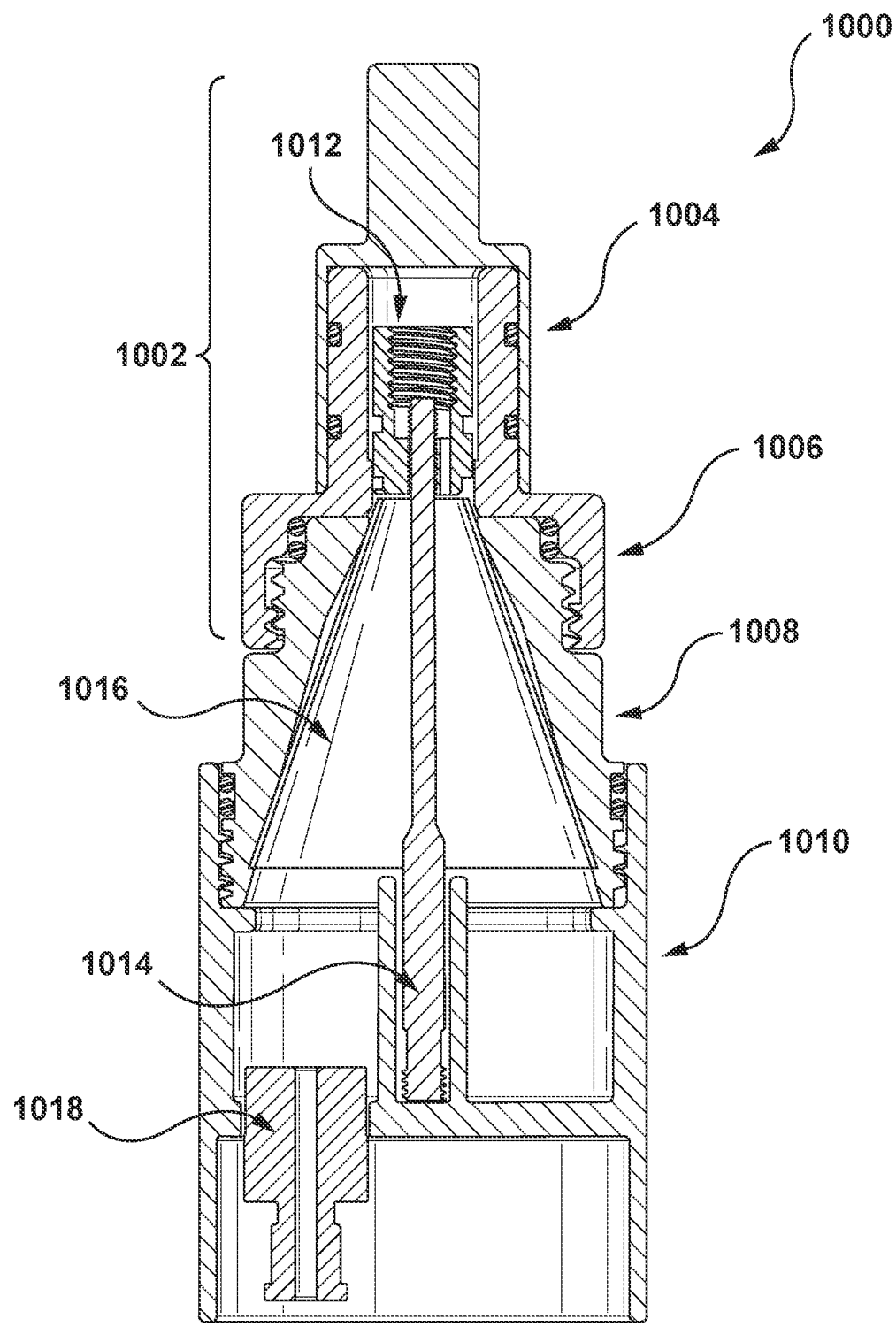
FIG. 10B depicts a cross-sectional illustration of the loading system of FIG. 10A, according to an embodiment hereof.

FIGS. 10A and 10B illustrate another example of a loading system 1000 in accordance with an embodiment hereof. One skilled in the art will realize that FIGS. 10A and 10B illustrate one example of a loading system and that existing components illustrated in FIGS. 10A and 10B may be removed and/or additional components may be added to the loading system 1000.

As illustrated in FIG. 10A, the loading system 1000 includes a locking collar assembly 1002. The locking collar assembly 1002 includes a cap 1004 and a locking collar 1006. The loading system 1000 also includes a loading funnel 1008 and an integrated storage jar 1010. As illustrated in FIG. 10B, the loading system 1000 includes a device retainer 1012 and a nosecone pin 1014. The device retainer 1012 secures an implantable medical device 1016. When coupled to the loading system 1000, the device retainer 112 is positioned within the locking collar 1006 of the locking collar assembly 1002. The nosecone pin 1014 is coupled to the device retainer 1012 and extends through the loading funnel 1008. The loading system 1000 also includes a fluid port 1018.

The device retainer 1012 is coupled to the implantable medical device 1016. As described above, any type of implantable medical device that requires a conversion from an uncompressed state to a compressed state and that requires loading onto a delivery device can be utilized with the loading system 1000. In an embodiment, the implanted medical device 1016 can include components that are intended to repair or support systems of the human body, e.g., prosthetic heart valves including organic tissue coupled to self-expandable or balloon-expandable stents/frames. For example, the loading system 1000 can be utilized on implantable medical devices that are to be delivered transluminally, e.g., via a catheter, and need to be loaded onto or into a catheter. The stent/frame may be radially compressed to have a low profile and loaded into/onto a delivery device such that the heart valve prosthesis can be delivered through the vessels to a target location in a compressed state, and then expanded at the target location, by a self-expanding stent/frame or a balloon of the delivery device, for instance, to replace the native heart valve.

The loading system 1000 is configured to store the implantable medical device 1016 in a partially compressed or "loaded" state. That is, the loading funnel 1008 is configured to apply a force to the implantable medical device 1016 to partially compress the implantable medical device 1016 and maintain the implantable medical device 116 in the partially compressed state during storage. In embodiments, as further described below, the loading funnel 1008 is formed with a tapered interior chamber that maintains the implantable medical device 1016 in a partially compressed state and operates to further compress the implantable medical device 1016 when loading the implantable medical device 1016 onto a delivery device.

The locking collar assembly 1002 allows a delivery device, e.g., catheter, to be attached to device retainer 1012 within minimal interaction with the implantable medical device 1016. In embodiment, as further described below, a delivery device (or component of the delivery device) is inserted into the locking collar assembly 1002 and coupled to the device retainer 1012. To load the implantable medical device 1016, the device retainer 1012 is retracted into the delivery device. As the device retainer 1012 is retracted, the implantable medical device 116 is further compressed by the loading funnel 1008.

While not described in further details, the device retainer 1012, the nosecone pin 1014, and the implantable medical device 1016 can include the same components of device retainer 112, the nosecone pin 114, and implantable medical device 116, respectively, as described above.

Figure 11A:
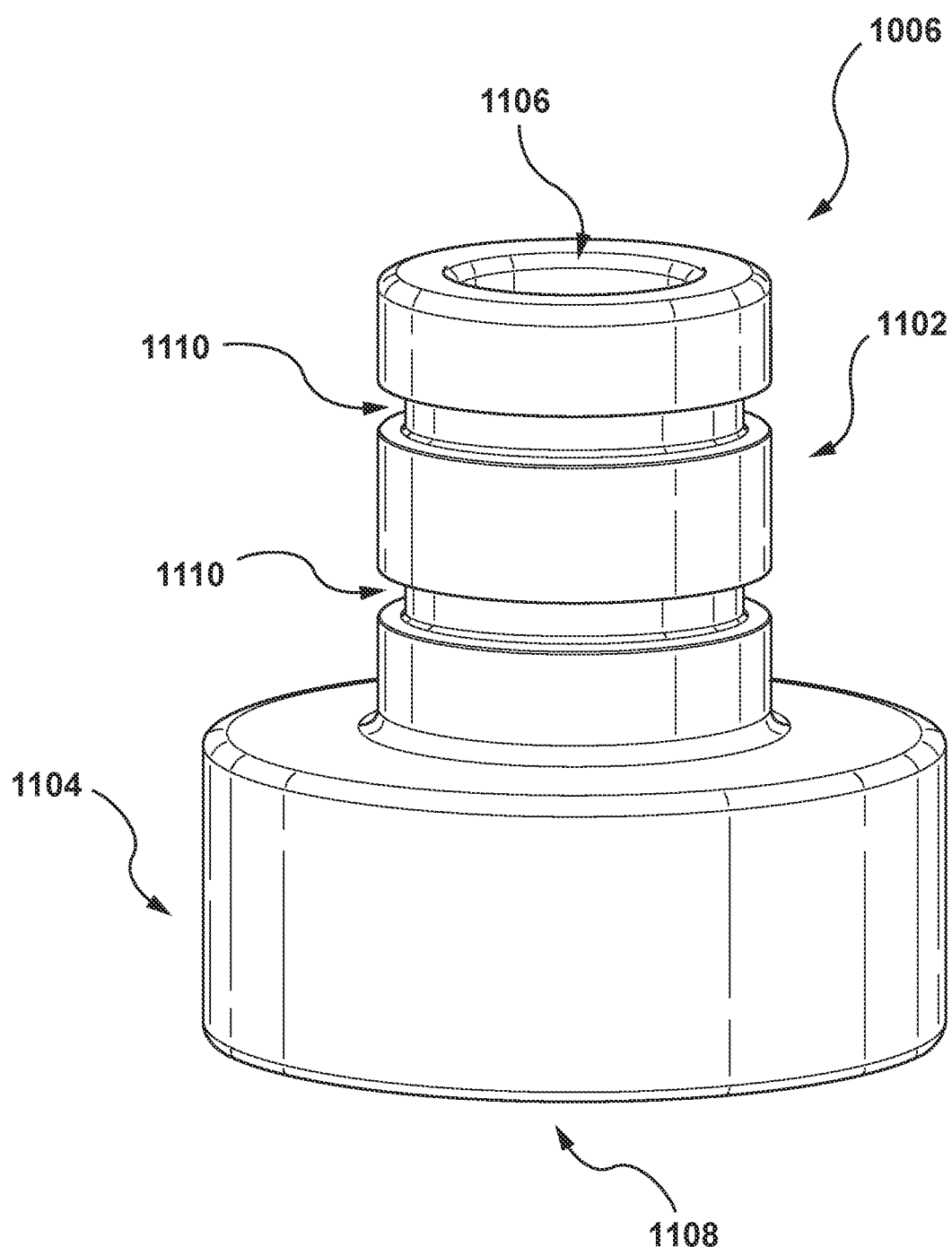
FIGS. 11A and 11B depict illustrations of a locking collar of the loading system of FIGS. 10A and 10B, according to an embodiment hereof.
Figure 11B:
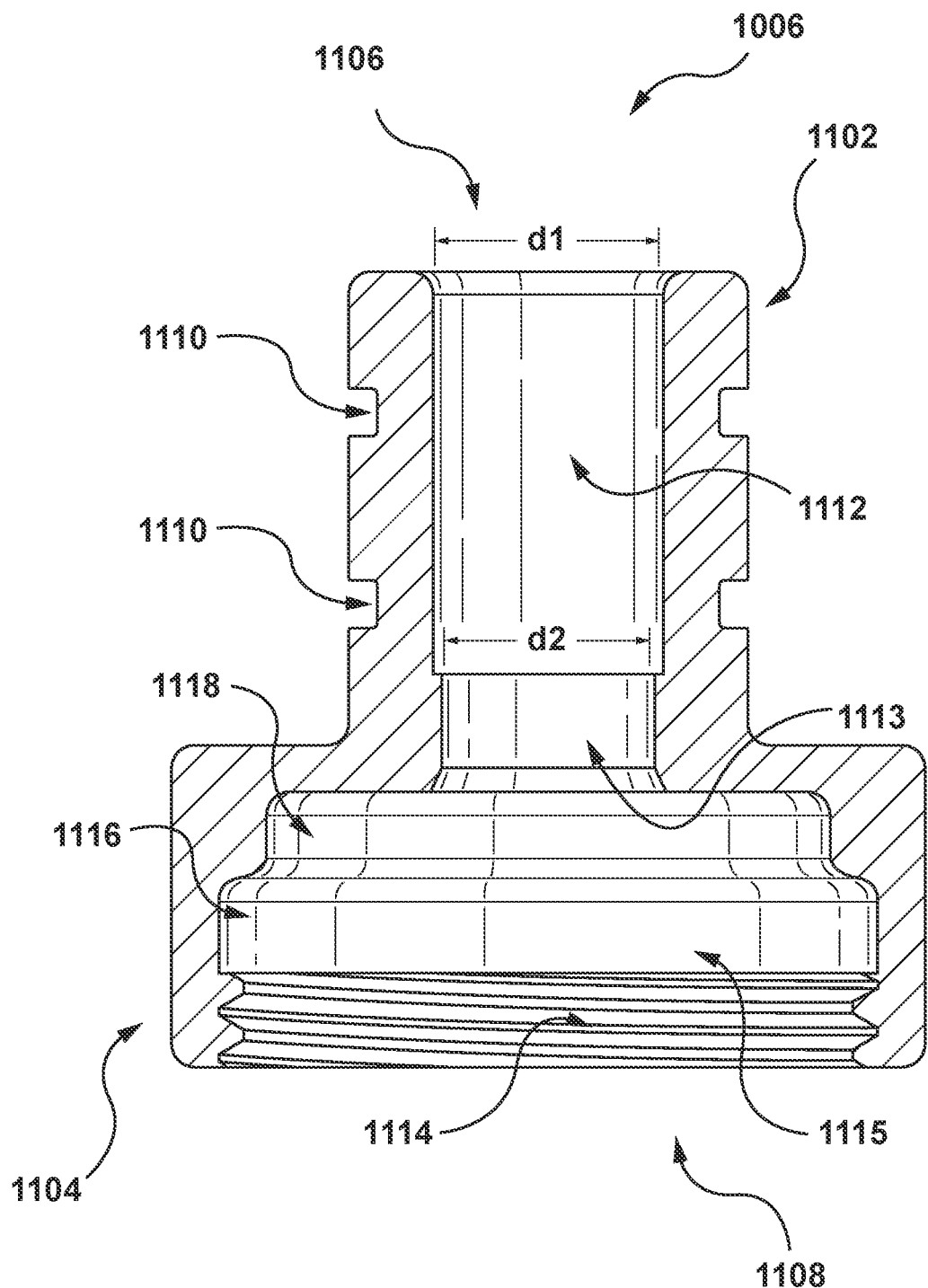

FIGS. 11A and 11B illustrate an example of a locking collar 1006 in accordance with an embodiment hereof. One skilled in the art will realize that FIGS. 11A and 11B illustrate one example of a locking collar and that existing components illustrated in FIGS. 11A and 11B may be removed and/or additional components may be added to the locking collar 1006.

As illustrated in FIG. 11A, the locking collar 1006 includes a locking collar neck 1102 and a locking collar base 1104. The locking collar 1006 includes a proximal opening 1106 located in the locking collar neck 1102 and a distal opening 1108 located in the locking collar base 1104. The locking collar neck 1102 includes circular channels 1110. The circular channel 1110 can be configured to receive sealing members, e.g., O-rings, that provide a fluid seal between the locking collar neck 1102 and the cap 1004.

As illustrated in FIG. 11B, the locking collar neck 1102 includes a loading channel 1112. The loading channel 1112 extends from the proximal opening 1106 to the top of the locking collar base 1104. The loading channel 1112 is formed in an approximate cylindrical shape with circular cross-section having an inner diameter, $d_1$. The loading channel 1112 is formed with the diameter, $d_1$, to accommodate the device retainer 1012 and allow the insertion of a delivery device, e.g., catheter, into the locking collar neck 1102. In embodiments, the diameter, $d_1$, of the loading channel 212 may depend on the FR size of the catheter. For example, the diameter, $d_1$, of the loading channel 212 may be formed to accommodate a 18-33 Fr catheter. In an embodiment, the delivery device may be inserted into the proximal opening 1106, and the device retainer 1012 may be positioned at or near the bottom of the locking collar neck 1102. The locking collar 1006 can be formed of any suitable material such as, but not limited to a polymeric material.

For example, the loading system 1000 may be configured to store and load a 42 millimeter (mm) TMVR device, e.g., heart valve and frame. In such as embodiment, the loading channel 1112 may be formed with a diameter, $d_1$, in a range of approximately 6 mm to approximately 13 mm. In another example, the loading system 1000 may be configured to store and load a 48 mm TMVR device. In such an embodiment, the loading channel 1112 may be formed with a diameter, $d_1$, in a range of approximately 6 mm to approximately 13 mm. One skilled in the art will realize that the loading channel 1112 can be formed to any dimension and/or cross-sectional shape to accommodate different medical devices and or delivery devices.

As illustrated in FIG. 11B, the locking collar neck 1102 also include a circular ridge 1113 positioned at a distal end of the loading channel 1112. The circular ridge 1113 extends radially inward from the inner surface of the locking collar neck 1002. In an embodiment, the circular ridge 1113 can be formed in an approximate ring and/or torus shape. The circular ridge 1113 is formed to a diameter, $d_2$, that is smaller than the diameter, $d_1$, of the loading channel 1112. In an embodiment, the circular ridge 1113 can be formed to a diameter, $d_2$, that is larger than the diameter of the device retainer 1012, but smaller than the outer diameter of the delivery device, e.g., an outer shaft of the delivery device, to be inserted into the locking collar neck 1102. In this embodiment, the circular ridge 1113 can function as a stop that prevents the delivery device from being inserted past the circular ridge 1113.

The locking collar base 1104 includes female threads 1114. The female threads 1114 are formed at a bottom portion of the locking collar base 1104 adjacent to the distal opening 1108. The female threads 1114 are configured to engage with threads of the loading funnel 1008 (described below in FIGS. 13A and 13B) to secure the loading funnel 1008 to the locking collar 1006. The locking collar base 1104 also include a cavity 1115. The cavity 1115 is formed of a first section 1116 that is positioned adjacent to or near the distal opening 1108 and a second section 1118 that is positioned adjacent to or near the distal end of the loading channel 1112. The first section 1116 and the second section 1118 are formed to a shape and dimension that matches the shape and dimensions of the loading funnel 1008, further described below.

Figure 12A:
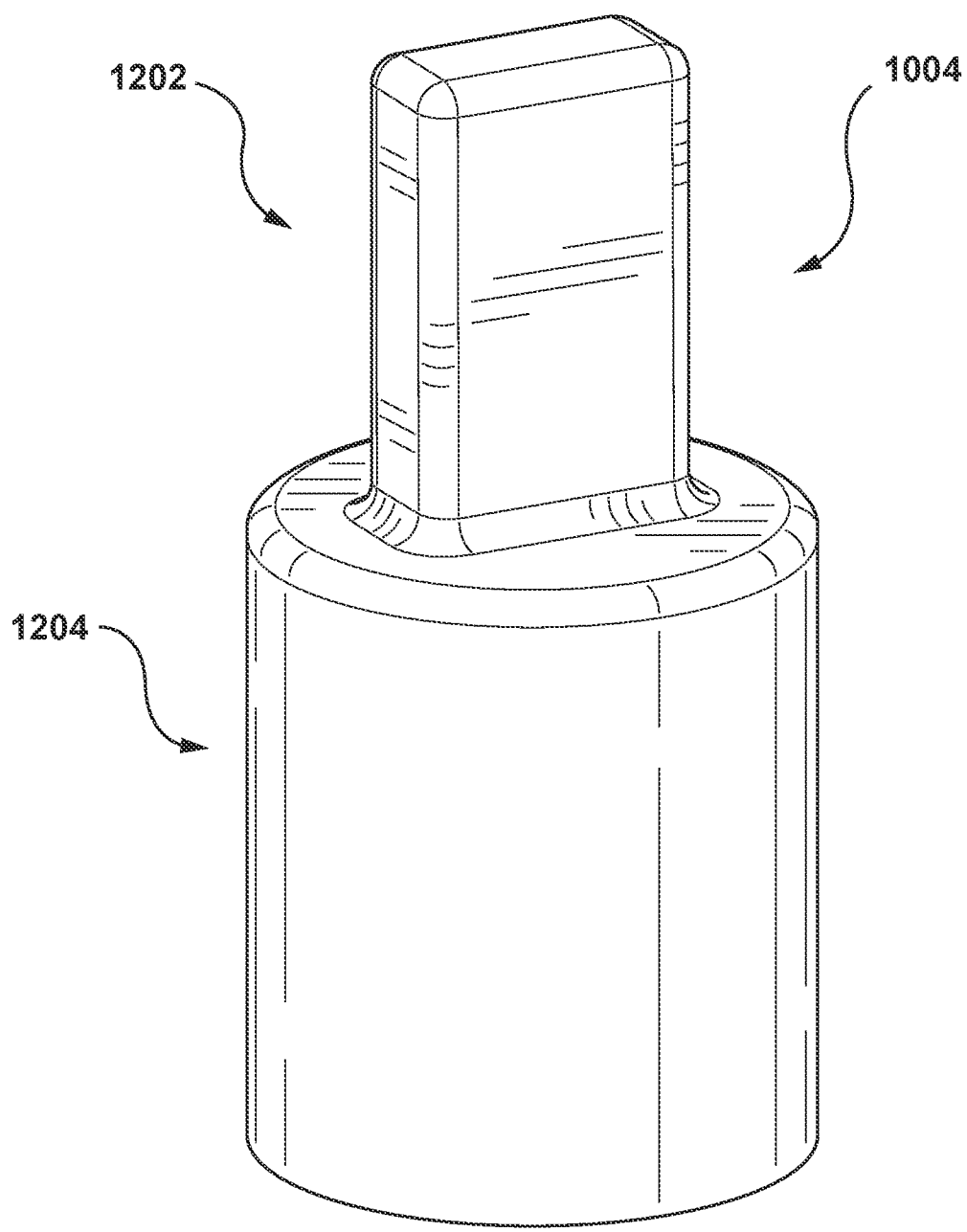
FIGS. 12A and 12B depict illustrations of a cap of the loading system of FIGS. 10A and 10B, according to an embodiment hereof.
Figure 12B:
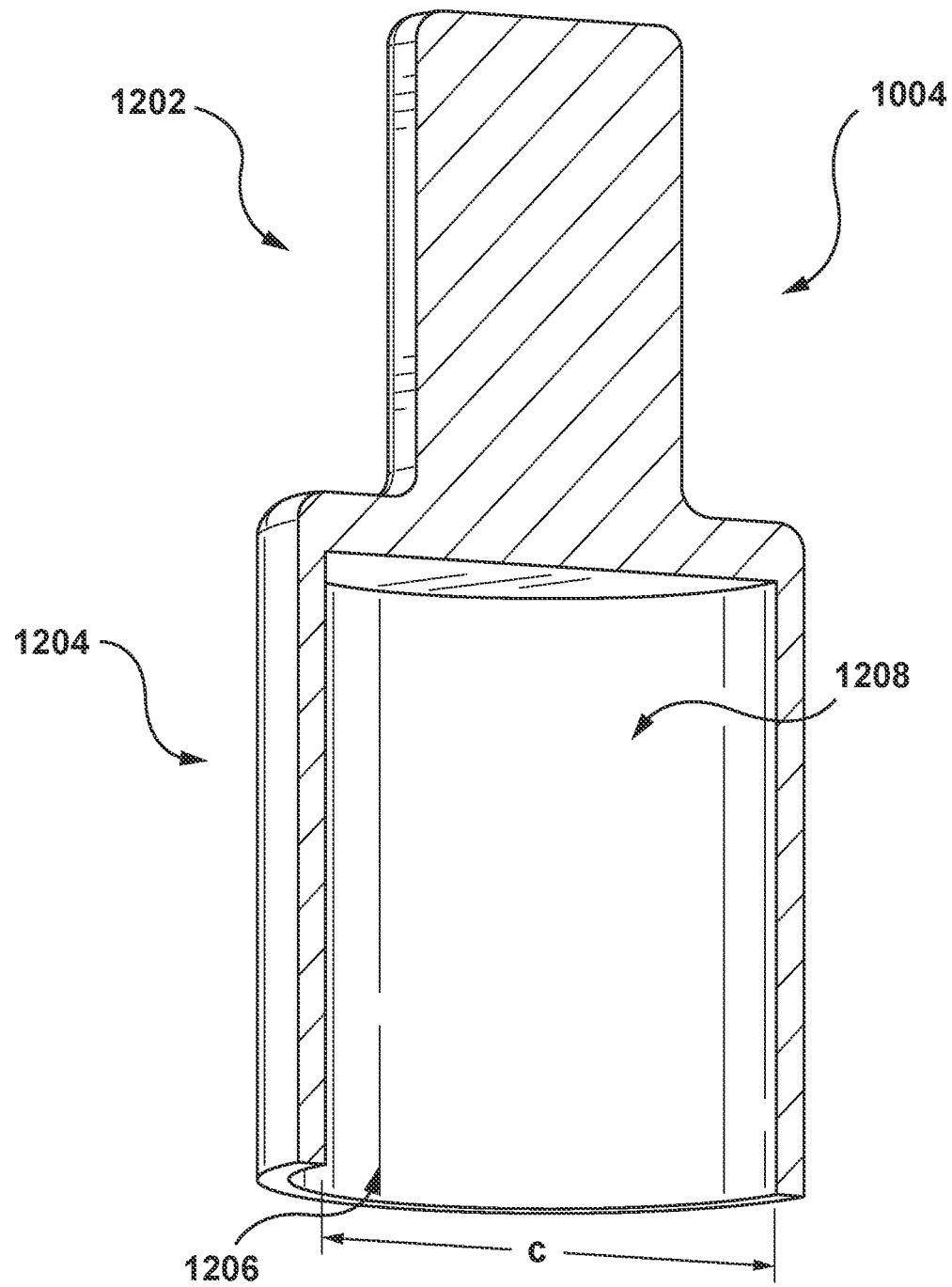

FIGS. 12A and 12B illustrate an example of the cap 1004 in accordance with an embodiment hereof. One skilled in the art will realize that FIGS. 12A and 12B illustrate one example of a cap and that existing components illustrated in FIGS. 12A and 12B may be removed and/or additional components may be added to the cap 1004.

As illustrated in FIG. 12A, the cap 1004 includes a cap neck 1202 and a cap base 1204. The cap neck 1202 is formed in an approximate rectangular polygon shape. As illustrated in FIG. 12B, the cap base 1204 include a cap opening 1206 that opens to a cap channel 1208. The cap channel 1208 in an approximate cylindrical shape with circular cross-section having a diameter, c, that is approximately equal or larger than an outer diameter of the cap neck 1202. For example, the cap channel 1208 may have the diameter, c, of approximately 15 mm and may have overall height of approximately 40 mm. As illustrated in FIGS. 10A and 10B above, the cap 1004 slides over the cap neck 1202 to provide a fluid seal to the loading channel 1112, e.g., via sealing members disposed in the circular channels 1110. The cap 1004 can be formed of any suitable material such as, but not limited to a polymeric material.

Figure 13A:
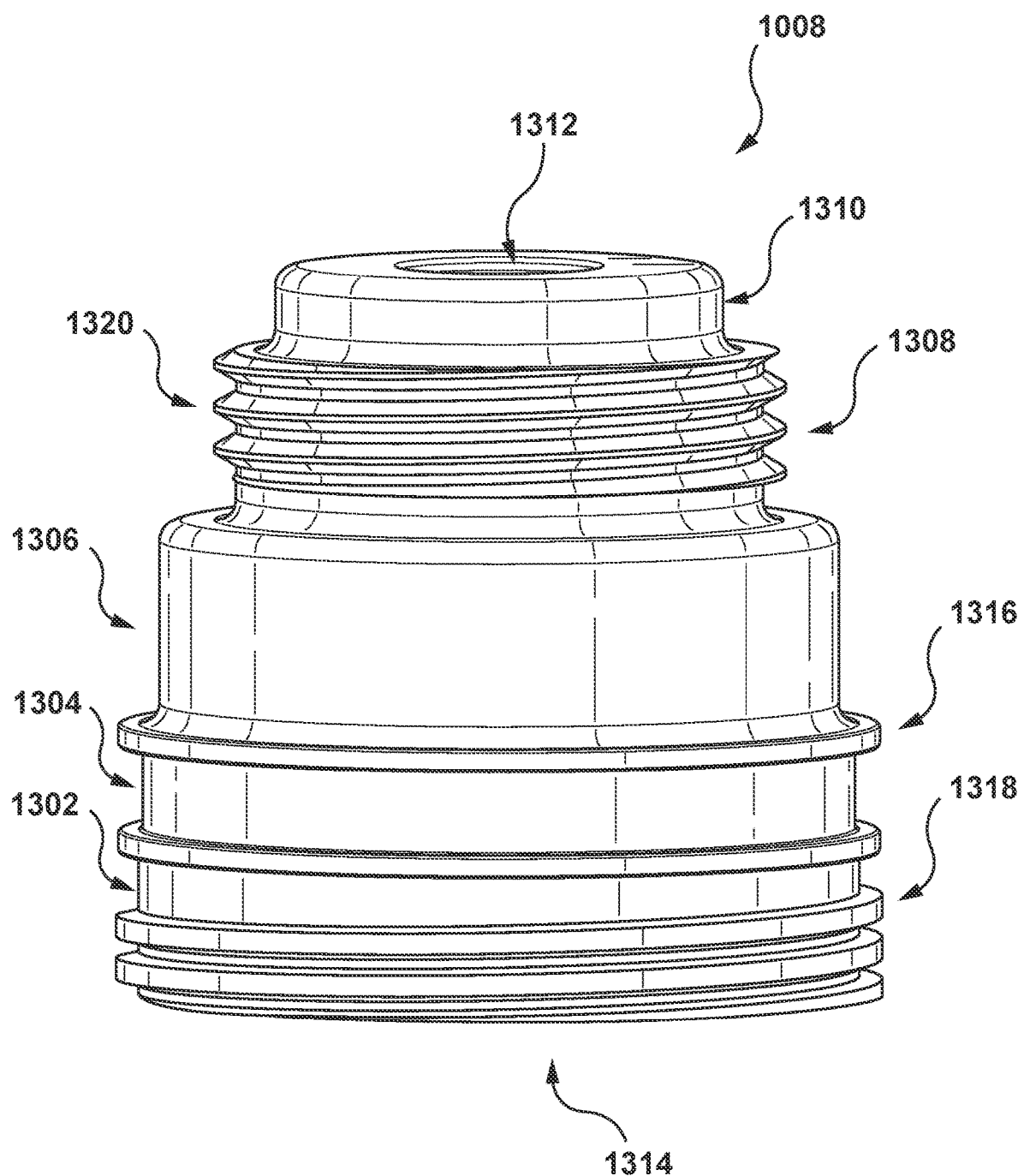
FIGS. 13A and 13B depict illustrations of a loading funnel of the loading system of FIGS. 10A and 10B, according to an embodiment hereof.
Figure 13B:
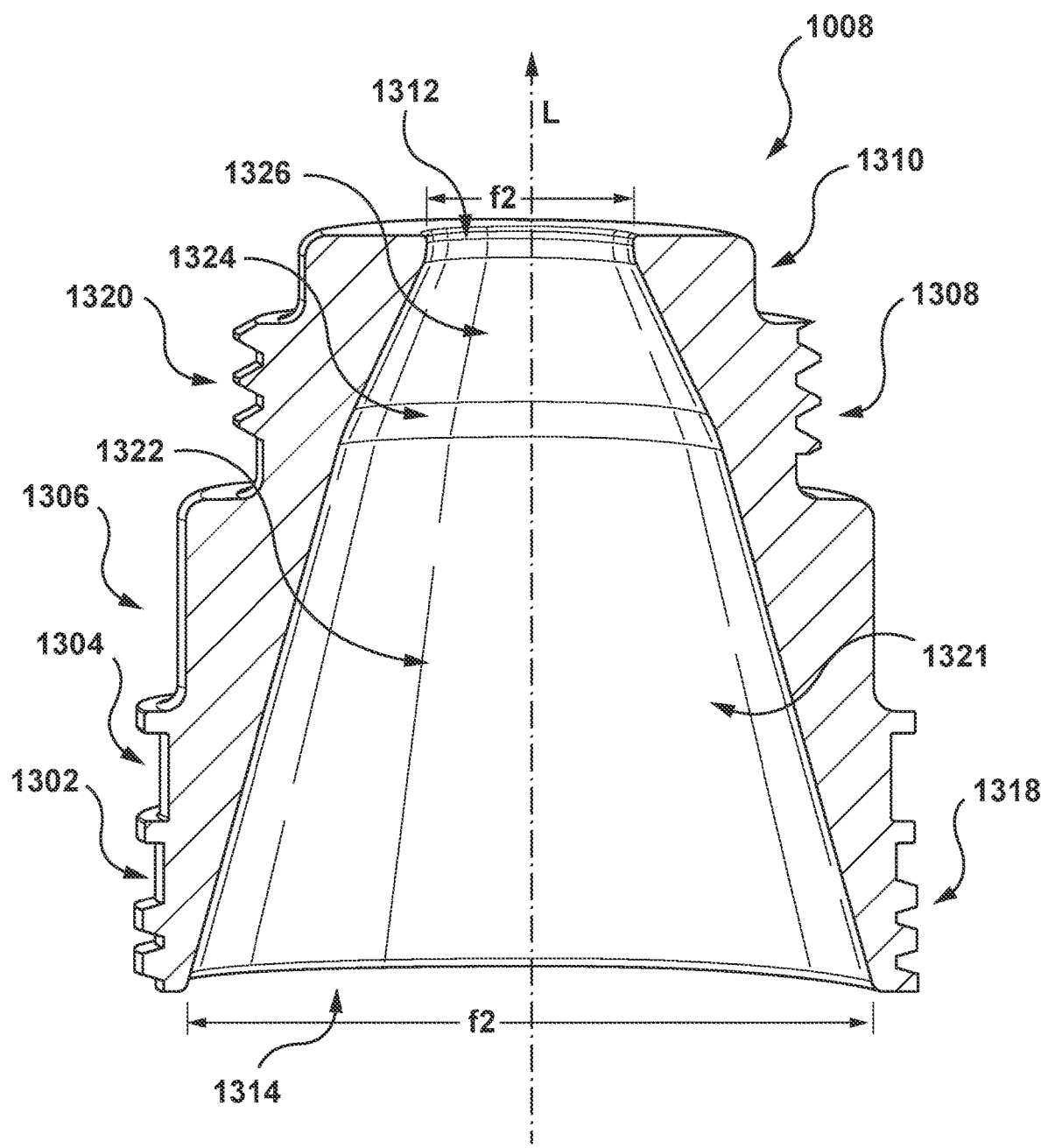

FIGS. 13A and 13B illustrate an example of the loading funnel 1008 in accordance with an embodiment hereof. One skilled in the art will realize that FIGS. 13A and 13B illustrate one example of a loading funnel and that existing components illustrated in FIGS. 13A and 13B may be removed and/or additional components may be added to the loading funnel 1008.

As illustrated in FIG. 13A, the loading funnel 1008 includes a first section 1302, a second section 1304, a third section 1306, a fourth section 1308, and a fifth section 1310. The loading funnel 1008 includes a proximal opening 1312 and a distal opening 1314. The loading funnel 1008 includes a ring 1316 that is formed at a proximal end of the second section 1304 and adjacent to and/or near the third section 1306. The ring 1316 is formed in a cylindrical shape that extends radially outward from the outer surface of the second section 1304. The loading funnel 1008 includes male threads 1318. The male threads 1318 are formed on the first section 1302 adjacent to and/or near the distal opening 1314. The male threads 1318 are configured to engage with threads of the integrated storage jar 1010 (described below in FIGS. 14A-14C) to secure the integrated storage jar 1010 to the loading funnel 1008. The ring 1316 can operate as a stop or seal when the integrated storage jar 1010 is attached to the loading funnel 1008. For example, the ring 1316 may contain one or large o-ring seals that may prevent the liquid from leaking out loading system 1000.

The loading funnel 1008 includes male threads 1320. The male threads 1320 are formed on the fourth section 1308 adjacent to and/or near the proximal opening 1312. The male threads 1320 are configured to engage with the female threads 1114 of the locking collar 1006 to secure the loading funnel 1008 to the locking collar 1006. The loading funnel 1008 can be formed on any suitable material such as, but not limited to stainless steel.

The loading funnel 1008 is formed in an approximate conical shape with the fifth section 1310 having a smaller diameter than the fourth section 1308 and the fourth section having a smaller diameter than the first section 1302, the second section 1304, and the third section 1306. As illustrated in FIG. 13B, the loading funnel 1008 forms a compression volume 1321 in the interior of the loading funnel 1008. The compression volume 1321 opens at the proximal opening 1312 and the distal opening 1314. The compression volume 1321 is formed of a first chamber 1322, a second chamber 1324, and a third chamber 1326. The proximal opening 1312 is formed in the fifth section 1310 having a diameter, $f_1$. The distal opening 1314 is formed in the first section 1302 having a diameter, $f_2$. The interior of the loading funnel 1008 forms the compression volume 1321. The compression volume 1321 is formed in an approximate funnel or cone shape with a decreasing volume from the first section 1302 to the fifth section 1310. In an embodiment, the compression volume 1321 is tapered, in a decreasing diameter, from diameter, $f_2$, at the distal opening 1314 to the diameter, $f_1$, at the proximal opening 1312. Each of the first chamber 1322, the second chamber 1324, and the third chamber 1326 can be formed in the shape of a funnel, each with a different degree of decreasing volume from the distal opening 1314 to the proximal opening 1312. In embodiments, the volume of the compression volume 1321 operates to maintain the implantable medical device 1016 in a partially compressed state.

In embodiments, the degree of decreasing volume, e.g., taper angle, can affect the angle at which the implant attachment tabs exit the funnel, with a longer taper improving the loading of the implantable medical device 116. The longer taper may provide a smoother transition for the implantable medical device 116 during loading into the delivery device. A short taper may apply compressive strain on the implantable medical device 116, may require high force during loading, may result in an uneven crimp, may cause inflooding of the implantable medical device 116, or may apply an additional compressive load on the implantable medical device 116 when stored. According the degree of decreasing volume, e.g., taper angle, may be set to minimize these and ensure integrity of the implantable medical device 116.

In embodiments, the decreasing volume of the compression volume 1321 also operates to apply a compression force on the implantable medical device 1016 as device retainer 1012 is retracted through the loading channel 1112. That is, as the device retainer 1012 is retracted into the delivery device positioned in the loading channel 1112, the implantable medical device 1016 retracts in a loading direction, L, through the proximal opening 1312. As the implantable medical device 1016 moves through the compression volume 1321, the inner surfaces of the loading funnel 1008 apply a compression force on surfaces of the implantable medical device 1016.

In embodiments, the diameter, $f_1$, of the proximal opening 1312 may depend on the FR size of the catheter. For example, the diameter, $f_1$, of the proximal opening 1312 may be formed to accommodate a 18-33 Fr catheter. In embodiments, the diameter, $f_2$, of the distal opening 1314 may depend on an outer diameter of the implantable medical device 116.

In some embodiments, the loading system 100 may be configured to store and load a 42 mm TMVR device, and In such an embodiment, the diameter, $f_1$, can be in a range of approximately 6 mm to approximately 13 mm, and the diameter, $f_2$, can be in the range of approximately 20 mm to approximately 60 mm.

For example, the loading system 1000 may be configured to store and load a 42 mm TMVR device, and the proximal opening 1312 may be formed with a diameter, $f_1$, and the distal opening 1314 may be formed with a diameter, $f_2$. In such an embodiment, the diameter, $f_1$, can be in a range of approximately 6 mm to approximately 13 mm, and the diameter, $f_2$, can be in the range of approximately 20 mm to approximately 60 mm. In another example, the loading system 1000 may be configured to store and load a 48 mm TMVR device, and the proximal opening 1312 may be formed with a diameter, $f_1$, and the distal opening 1314 may be formed with a diameter, $f_2$. In such an embodiment, the diameter, $f_1$, can be in a range of approximately 6 mm to approximately 13 mm, and the diameter, $f_2$, can be in the range of approximately 20 mm to approximately 60 mm. One skilled in the art will realize that the compression volume 1321 can be formed to any dimension and/or cross-sectional shape to accommodate different medical devices and or delivery devices.

While FIGS. 11A, 11B, 13A, and 13B illustrate threads for coupling the locking collar 1006 and the loading funnel 1008, one skilled in the art will realize that other types of connectors can be utilized to mechanically couple the locking collar 1006 and the loading funnel 1008. In some embodiments, the locking collar 1006 and the loading funnel 1008 can include a push fit locking collar that acts as an interference fit for coupling the locking collar 1006 and the loading funnel 1008. For example, an outer diameter of the locking collar 1006 may be larger than an inner diameter of the loading funnel 1008. In some embodiments, the locking collar 1006 and the loading funnel 1008 can include a c-clip mechanism connector that acts as a mechanical interference between the locking collar 1006 and the loading funnel 1008. In some embodiments, the locking collar 1006 and the loading funnel 1008 can include a snap fit connection (e.g., cantilever, torsional and/or annular). For example, the locking collar 1006 can include a protruding edge or tab, and the loading funnel 1008 can include a snap-in area (e.g., groove, channel, etc.) for receiving and locking the protruding edge or tab. Likewise, for example, the loading funnel 1008 can include a protruding edge or tab, and the locking collar 1006 can include a snap-in area (e.g., groove, channel, etc.) for receiving and locking the protruding edge or tab.

Figure 14A:
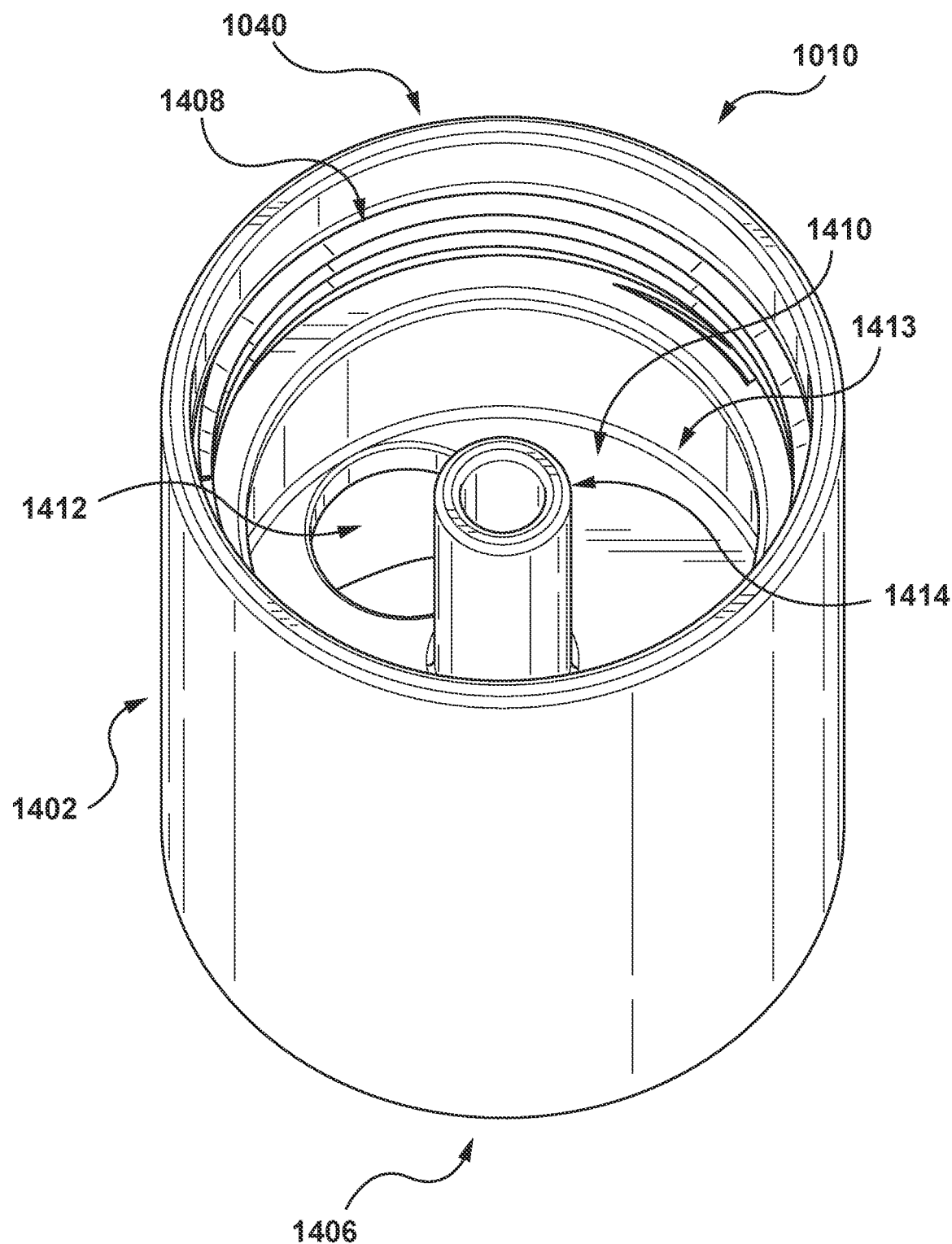
FIGS. 14A-14C depict several illustrations of a storage jar of the loading system of FIGS. 10A and 10B, according to an embodiment hereof.
Figure 14B:
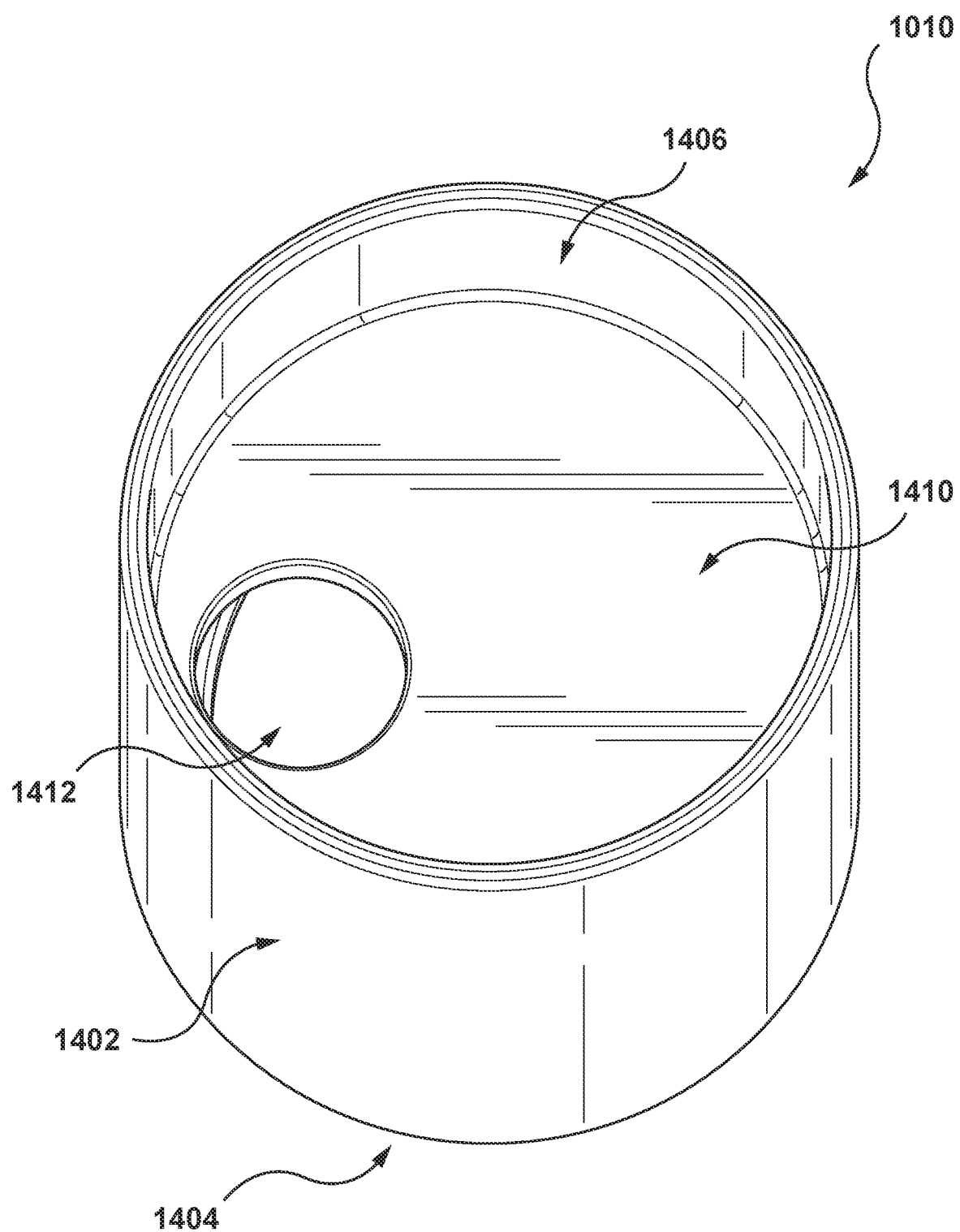
Figure 14C:
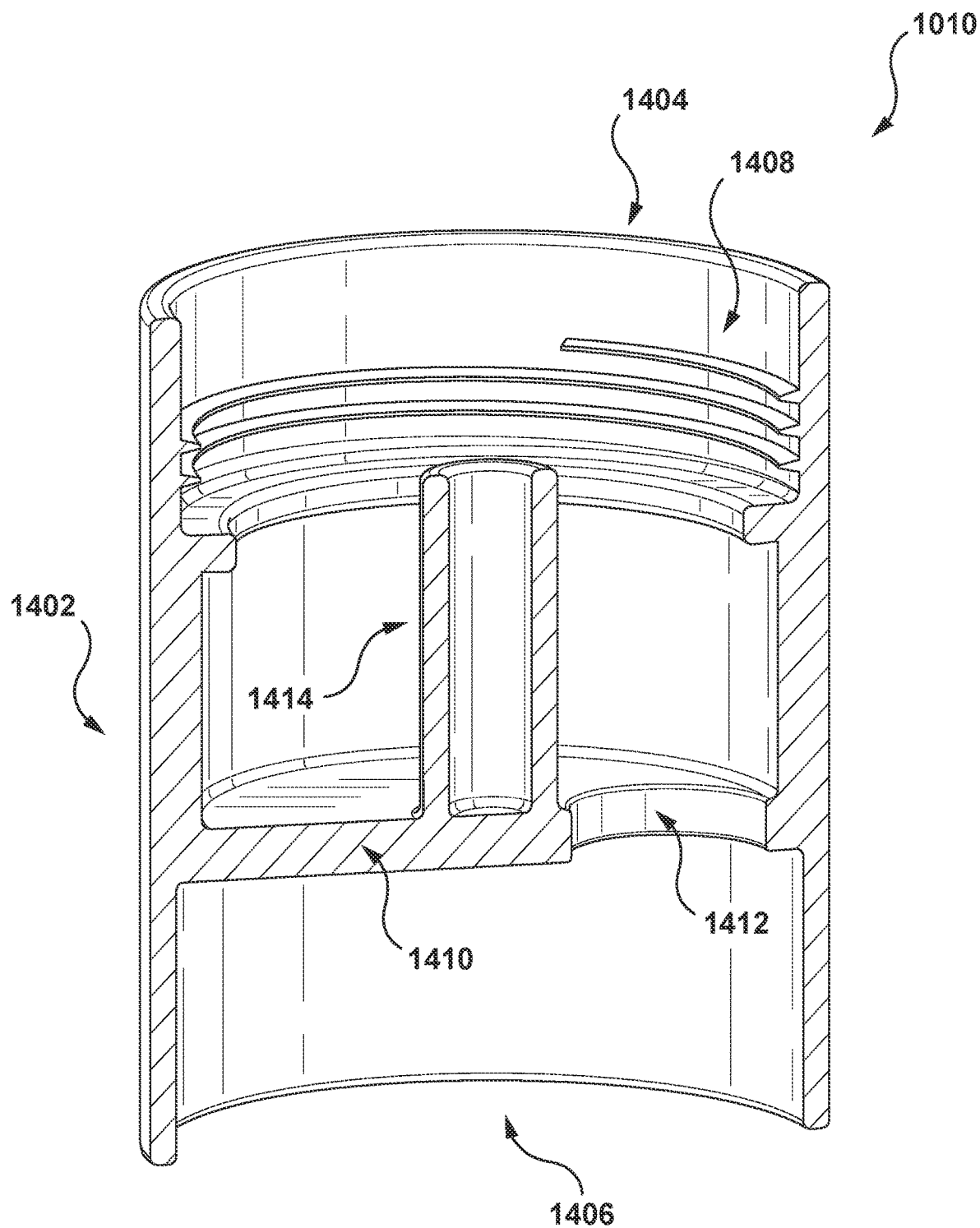

FIGS. 14A-14C illustrate an example of the integrated storage jar 1010 in accordance with an embodiment hereof. One skilled in the art will realize that FIGS. 14A-14C illustrate one example of an integrated storage jar and that existing components illustrated in FIGS. 14A-14C may be removed and/or additional components may be added to the integrated storage jar 1010.

As illustrated in FIG. 14A, the integrated storage jar 1010 includes a jar body 1402. The jar body 1402 is formed with an approximate cylindrical shape. The jar body 1402 includes a proximal opening 1404 and a distal opening 1406. The integrated storage jar 1010 includes female threads 1408. The female threads 1408 are formed at the proximal end of the jar body 1402 adjacent to or near the proximal opening 1404. The female threads 1408 are configured to engage with the male threads 1318 of the loading funnel 1008 to secure the integrated storage jar 1010 to the loading funnel 1008. The integrated storage jar 1010 can be formed of any suitable material such as, but not limited to a polymeric material.

The integrated storage jar 1010 includes a jar base 1410. The jar base 1410 includes an opening 1412. The opening 1412 is configured to receive the fluid port 1018. When the fluid port 1018 is inserted into the opening 1412, the jar base 1410 forms a fluid chamber 1413. The fluid chamber 1413 is configured to hold and maintain fluids within the loading system 1000, for example, preservation fluids and/or sterile fluids.

The integrated storage jar 1010 includes a nosecone pin holder 1414. The nosecone pin holder 1414 is configured to receive the nosecone pin 1014 and secure the nosecone pin 1014 in place when the integrate storage jar 1010 is attached to the loading funnel 1008. The nosecone pin holder 1414 is formed in an approximate cylindrical shape. The nosecone pin holder 1414 is configured to hold the nosecone pin 1014 in place and prevent movement of the nosecone pin 1014. That is, when the nosecone pin 114 is stored within the loading system 1000, the nosecone pin 114 abuts a bottom surface of the nosecone pin holder 1414. The sidewalls of the nosecone pin holder 1414 hold the nosecone pin 114 in position and prevent the nosecone pin 114 from moving laterally within the loading system 1000.

In embodiments, the nosecone pin holder 1414 operates to prevent the device retainer 1012 and the implantable medical device 1016 from exiting the distal opening 1314 of the loading funnel 1008. That is, the nosecone pin holder 1414 (e.g., bottom surface) applies a force on the nosecone pin 1014, which is attached to the device retainer 1012, to prevent the device retainer 1012 and the implantable medical device 1016 from sliding out of the loading funnel 1008 due to compression force of the loading funnel 1008 when the implantable medical device 1016 is in a partially compressed state.

While FIGS. 13A, 13B, and 14A-14C illustrate threads for coupling the loading funnel 1008 and the integrated storage jar 1010, one skilled in the art will realize that other types of connectors can be utilized to mechanically couple the loading funnel 1008 and the integrated storage jar 1010. In some embodiments, the loading funnel 1008 and the integrated storage jar 1010 can include a push fit locking collar that acts as an interference fit for coupling the loading funnel 1008 and the integrated storage jar 1010. For example, an outer diameter of the loading funnel 1008 may be larger than an inner diameter of the integrated storage jar 1010. In some embodiments, the loading funnel 1008 and the integrated storage jar 1010 can include a c-clip mechanism connector that acts as a mechanical interference between the loading funnel 1008 and the integrated storage jar 1010. In some embodiments, the loading funnel 1008 and the integrated storage jar 1010 can include a snap fit connection (e.g., cantilever, torsional and/or annular). For example, the loading funnel 1008 can include a protruding edge or tab, and the integrated storage jar 1010 can include a snap-in area (e.g., groove, channel, etc.) for receiving and locking the protruding edge or tab. Likewise, for example, the integrated storage jar 1010 can include a protruding edge or tab, and the loading funnel 1008 can include a snap-in area (e.g., groove, channel, etc.) for receiving and locking the protruding edge or tab.

Figure 15A:
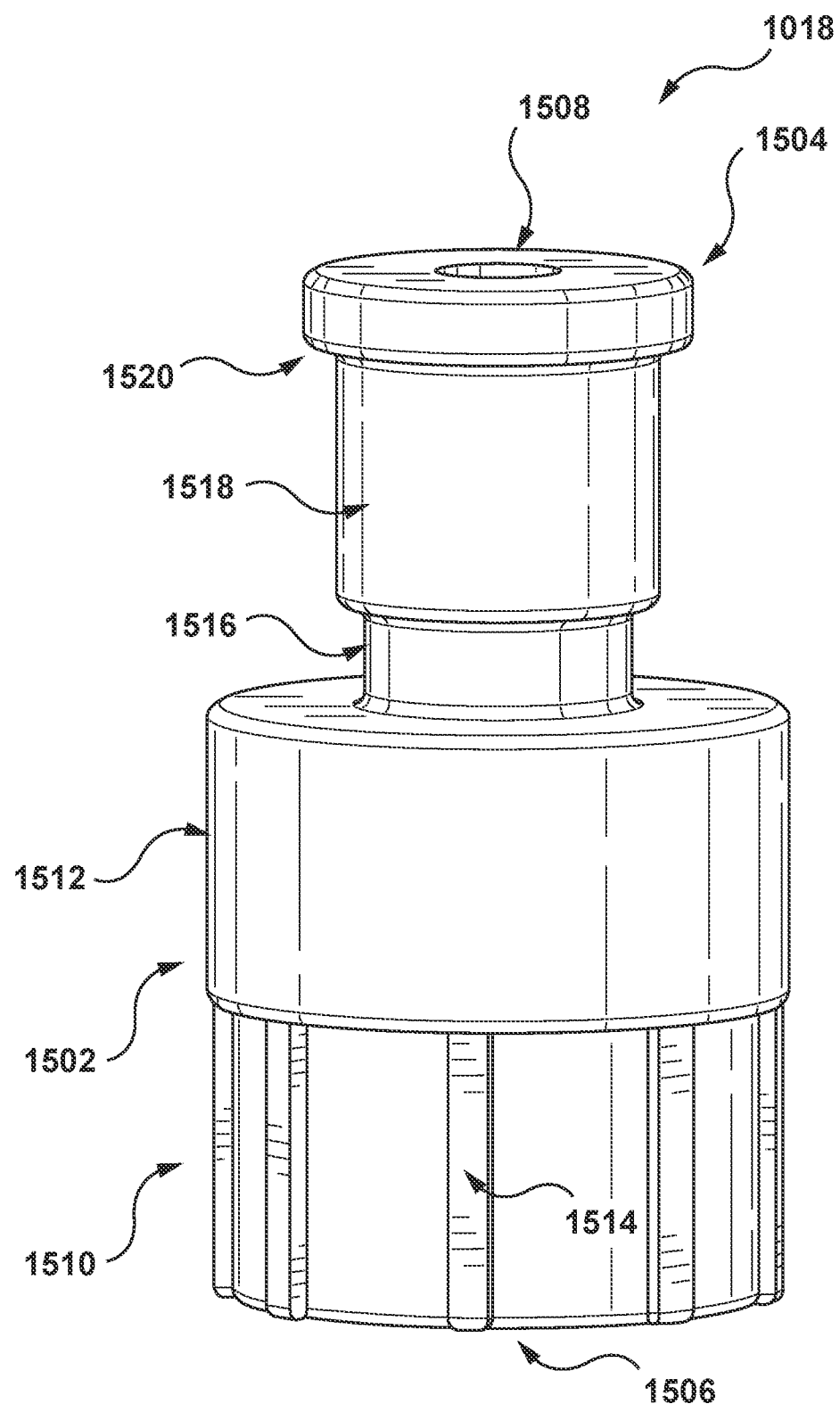
FIGS. 15A and 15B depict illustrations of a fluid port of the loading system of FIGS. 10A and 10B, according to an embodiment hereof.
Figure 15B:
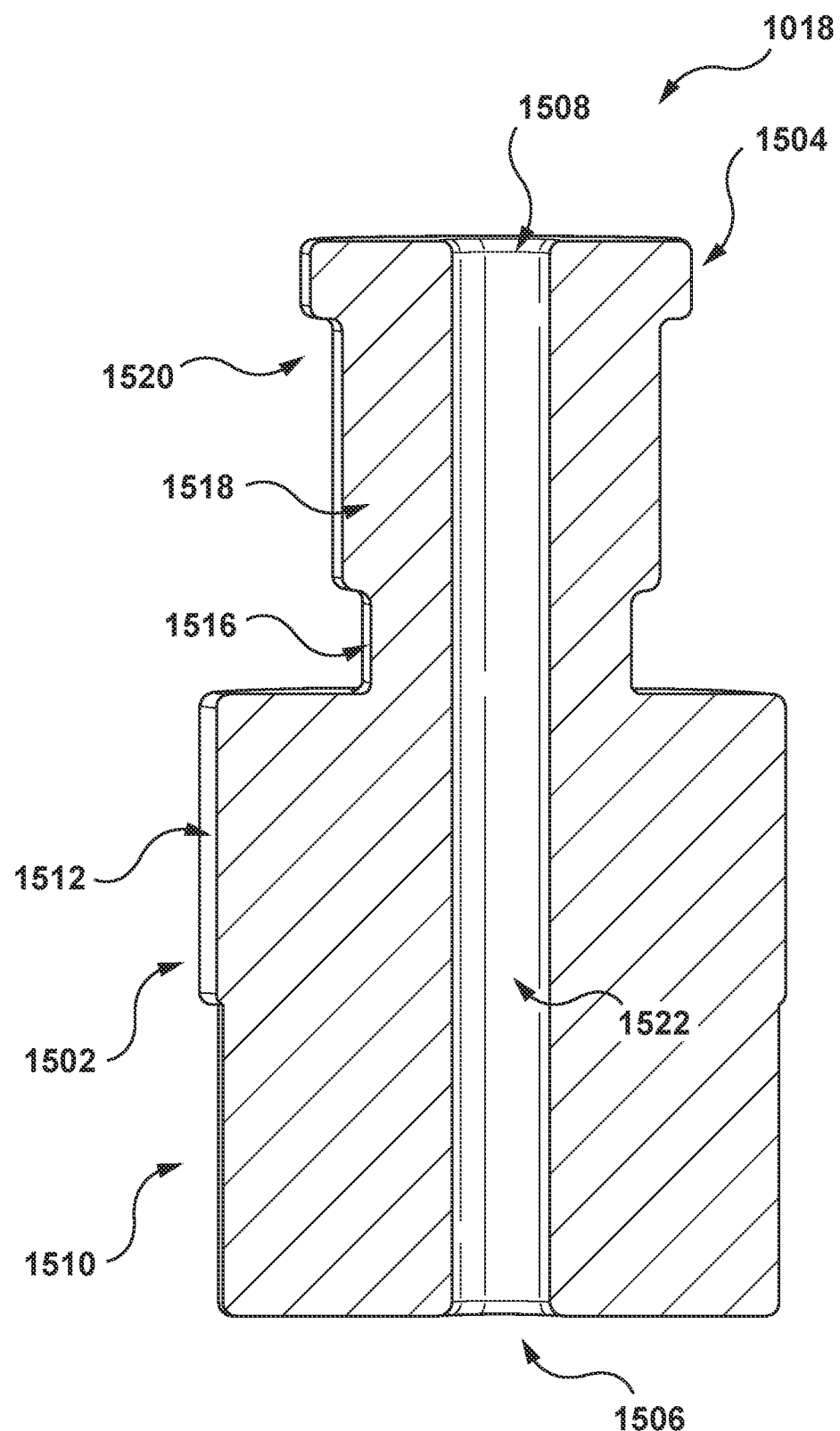
Figure 16:
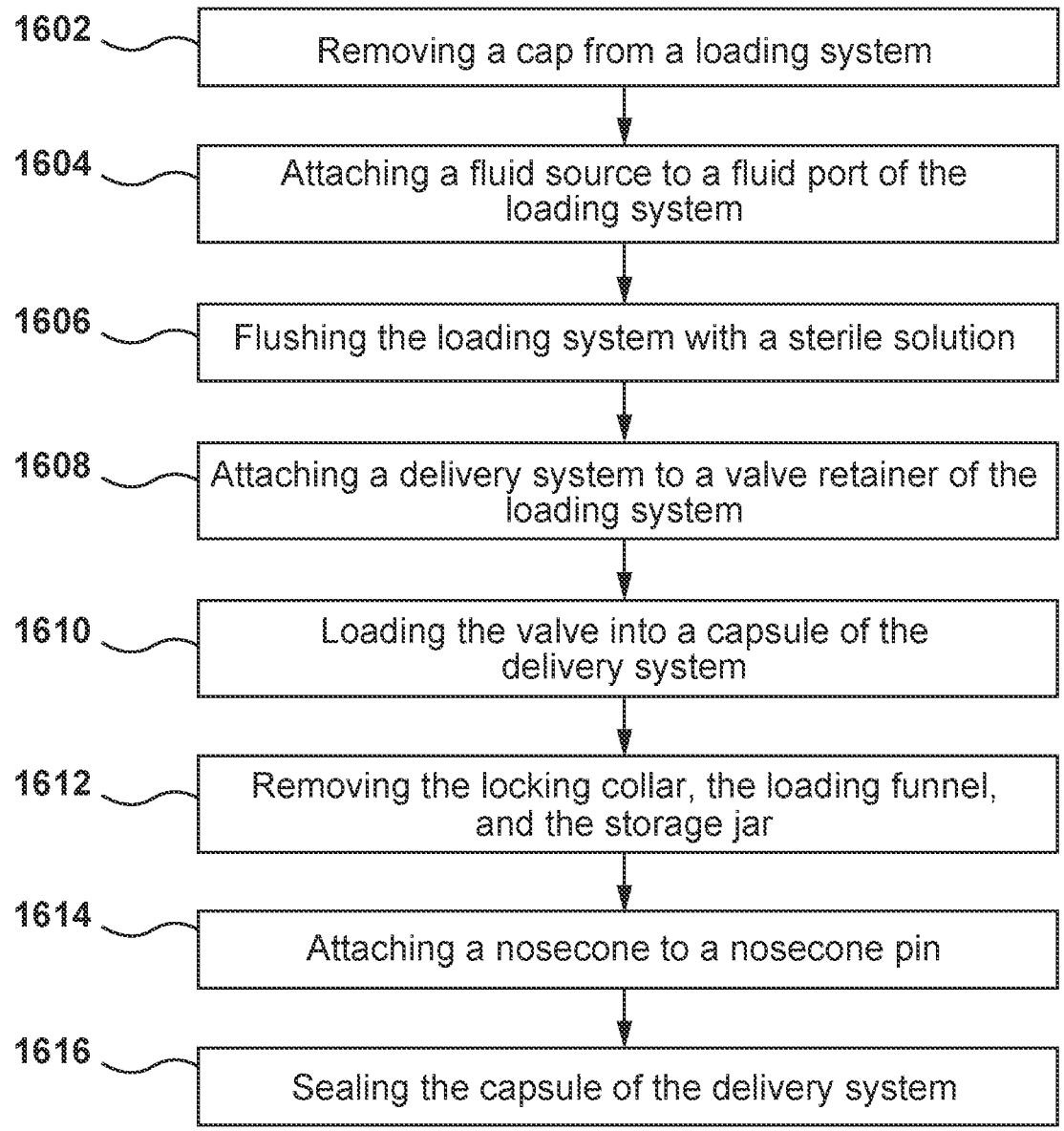
FIG. 16 depicts a flowchart of a process for the operation of the loading system of FIGS. 10A and 10B, according to an embodiment hereof.

FIGS. 15A and 15B illustrate an example of the fluid port 1018 in accordance with an embodiment hereof. One skilled in the art will realize that FIGS. 15A and 15B illustrate one example of a fluid port and that existing components illustrated in FIGS. 15A and 15B may be removed and/or additional components may be added to the fluid port 1018.

In embodiments, the fluid port 1018 can operate as a Luer connector to allow for syringe attachment. As illustrated in FIG. 15A, the fluid port 1018 includes a port base 1502 and a port neck 1504. The port base 1502 is formed in an approximate cylindrical shape and includes a proximal opening 1506 formed at a proximal end of the fluid port 1018. The port neck includes a distal opening 1508 formed at a distal end of the port neck. The port base 1502 includes a first base section 1510 that is formed adjacent to the proximal end of the fluid port 1018 and a second base section 1512 that is formed adjacent to the first base section 1510 and the distal end of the port base 1502. The port base 1502 also includes ridges 1514. The ridges 1514 operate to secure the fluid port 1018 into the opening 1412 of the integrated storage jar 1010. For example, the ridges 1514 can secure the fluid port 1018 into the opening 1412 via a friction force. In other embodiments, the fluid port 1018 can be secured to the opening 1412 using other types of connections such as adhesive, weld bond, or threaded/screw connection.

The port neck 1504 includes a first neck section 1516 that is formed adjacent to the port base 1502, a second neck section 1518 that is formed adjacent to the first neck section 1516, and a third neck section 1520 that is formed adjacent to the second neck section 1518 and the distal end of the fluid port 1018. Each of the first neck section 1516, second neck section 1518, and third neck section 1520 are formed in an approximate cylindrical shape.

As illustrated in FIG. 15B, the fluid port 1018 includes a fluid channel 1522. The fluid channel 1522 extends from the proximal opening 1506 to the distal opening 1508. The fluid channel 1522 allows fluid to be injected for extracted from the loading system 1000. For example, a fluid delivery device, e.g., syringe, can be attached to the fluid port 1018 to extract and inject fluids.

In embodiments, the implantable medical device 1016 can be loaded into the loading system 1000. For example, the implantable medical device 1016 can be coupled to the device retainer 1012, and the nosecone pin 1014 can be secured to the device retainer 1012 by engaging the male threads of the nosecone pin 1014 and the female threads of the device retainer 1012. The device retainer 1012 including the implantable medical device 1016 and the nosecone pin 1014 can be inserted into the loading funnel 1008 and locking collar assembly 1002 (attached to the loading funnel 1008) to partially compress the implantable medical device 1016. For example, the device retainer 1012 can be inserted into the distal opening 1314 of the loading funnel 1008 and retracted through the loading funnel 1008 into the loading channel 1112 of the locking collar 1006. The integrate storage jar 1010 can then be coupled to the loading funnel 1008 by engaging the female threads 1408 of the integrate storage jar 1010 with the male threads 1318 of the loading funnel 1008.

In embodiments, once the implantable medical device 1016 is loaded into the loading system 1000, the loading system 1000 may be stored for a period of time until the implantable medical device 1016 is utilized in a procedure. The loading system 100 can be filed with a preserving fluid via the fluid port 1018 in the integrated storage jar 1010. The preserving fluid can be any type of fluid that maintains the integrity and quality of the loading system 1000. For example, if the implantable medical device 1016 include organic material, the preserving fluid may include formaldehyde to maintain the integrity of the organic material.

FIG. 16 and FIGS. 17A-17I illustrate an example of a process 1600 for the operation of the loading system 1600 of FIGS. 10A and 10B for loading an implantable medical device into a delivery system. While FIG. 16 and FIGS. 17A-17I illustrate various operations that can be performed in the process 1600, one skilled in the art will realize that existing operations can be removed and additional operations can be added. Likewise, one skilled in the art will realize that the order of the operations can be changed.

In 1602, the process 1600 includes removing a cap from a loading system. For example, as illustrated in FIGS. 17A and 17B, the cap 1004 can be removed from the loading system 1000. For example, a force can be applied to the cap 1004 to extract the cap 1004 from the locking collar neck 1102.

In 1604, the process 1600 includes attaching a fluid source to a fluid port of the loading system. In 1606, the process 1600 includes flushing the loading system with a sterile solution. For example, as illustrated in FIG. 17C, a syringe 1702 can be attached to the fluid port 1018 of the loading system 1000. The syringe 1702 can then be operated to introduce a sterile solution, e.g., saline, into the loading system 1000 via the fluid channel 1522. The saline can replace the preserving fluid contained with the loading system and wash the interior of the loading system 1000.

In 1608, the process 1600 includes attaching a delivery device to a device retainer of the loading system. For example, as illustrated in FIG. 17D, a delivery device 1704 can be attached to the device retainer 1012. The delivery device 1704 can include an outer shaft and an inner shaft that retracts into a lumen of the inner shaft. The inner shaft can include male threads that engage with the female threads of the device retainer 1012. The outer shaft can be inserted into the locking collar neck 1102. The inner shaft can be extended from the outer shaft and can be attached the device retainer 1012, e.g., screwed into.

In 1610, the process 1600 includes loading the valve into a capsule of the delivery device. In embodiments, the capsule can be the distal portion of the outer shaft of the delivery device 1704. As illustrated in FIGS. 17E and 17G, the inner shaft can be retracted into the outer shaft. As the inner shaft is retracted, the device retainer 1012 is also retracted into the outer shaft. Simultaneously, the implantable medical device 1016 is retracted in the loading direction, L, through the loading funnel 1008. As the implantable medical device 1016 moves through the compression volume 1321, the inner surfaces of the loading funnel 1008 apply a compression force on surfaces of the implantable medical device 1016. As the inner shaft is retracted, additional sterile solution may be injected into the loading system 1000 with the syringe 1702.

In 1612, the process 1600 includes removing the locking collar, the loading funnel, and the storage jar. As illustrated in FIG. 17 locking collar neck 1102, e.g., sliding the outer shaft from the locking collar neck 1102.

In 1614, the process 1600 includes attaching a nosecone to a nosecone pin. For example, as illustrated in FIG. 17H, a nosecone 1706 can be attached to the nosecone pin, for example, by engaging the male threads with female threads of the nosecone 1706.

In 1616, the process 1600 includes sealing the capsule of the delivery device. For example, as illustrated in FIG. 17I, the inner shaft can be further retracted into the outer shaft until the nosecone 1706 engages and creates a seal with the outer shaft.

Additional discussion of various embodiments is presented below:

Embodiment 1 is a device for storing medical devices and loading the medical devices onto delivery devices. The device includes a locking collar assembly including a proximal end, a distal end, and a loading channel formed between the proximal end and the distal end. The device also includes a loading funnel coupled to the distal end of the locking collar assembly at a proximal end of the loading funnel. The loading funnel is configured to store a collapsible medical device within a tapered interior volume of the loading funnel in a partially collapsed state. The tapered interior volume decreases in volume from a distal end of the loading funnel to the proximal end of the loading funnel. The device includes a retainer positioned with the loading channel at the distal end of the locking collar assembly and includes a connector configured to couple to a delivery device. The collapsible medical appliance is coupled to the retainer. The retainer maintains the collapsible medical device within the loading funnel prior to connection to the delivery device. The device further includes a nosecone pin coupled to the retainer and positioned within the tapered interior volume of the loading funnel. Additionally, the device includes a storage jar coupled to a distal end of the loading funnel. The storage jar is configured retain the collapsible medical device and the nosecone pin within the tapered interior volume of the loading funnel.

Embodiment 2 includes the device of embodiment 1, and further includes a cap removably coupled to locking collar assembly, wherein the cap and the storage jar maintain fluids within an interior volume of the of the storage jar, the tapered interior volume of the loading funnel, and the loading channel of the locking collar assembly.

Embodiment 3 includes the device embodiment 2, wherein the locking collar assembly includes: a locking collar neck configured to receive the cap; and a locking collar body comprising female threads formed on an interior surface of the locking collar body.

Embodiment 4 includes the device of embodiment 3, wherein the loading funnel includes: male threads formed at the proximal end of the loading funnel, wherein the male threads are configured to engage the female threads of the locking collar body, and male threads formed at the distal end of the loading funnel.

Embodiment 5 includes the device of embodiment 4, wherein the storage jar includes: female threads formed at a proximal end of the storage jar, wherein the female threads are configured to engage the male threads formed at the distal end of the loading funnel to secure the storage jar to the loading funnel; and one or more fluid ports configured to selectively allow fluid to flow into and out of an interior volume of the storage jar and the loading funnel.

Embodiment 6 includes the device of any of embodiments 1-5, wherein the tapered interior volume comprises an approximate conical shape.

Embodiment 7 includes the device of any of embodiments 1-6, wherein the connector of the retainer comprises female threads configured to engage male threads of the delivery device.

Embodiment 8 includes the device of any of embodiments 1-7, wherein the collapsible medical device is an expanding frame containing a heart valve.

Embodiment 9 is a device for storing medical devices and loading the medical devices onto delivery devices. The device includes a locking collar assembly including a proximal end, a distal end, and a loading channel formed between the proximal end and the distal end. The device also includes a loading funnel coupled to the distal end of the locking collar assembly at a proximal end of the loading funnel. The loading funnel is configured to store a collapsible medical device in a partially collapsed state within a tapered interior volume of the loading funnel. The tapered interior volume decreases in volume from a distal end of the loading funnel to the proximal end of the loading funnel. Further, the device includes a retainer positioned with the loading channel at the distal end of the locking collar assembly and includes a connector configured to couple to a delivery device. The collapsible medical device is coupled to the retainer. The retainer maintains the collapsible medical device within the loading funnel prior to connection to the delivery device. The device includes a nosecone pin coupled to the retainer and positioned within the tapered interior volume of the loading funnel. Additionally, the device includes a funnel cap coupled to the distal end of the loading funnel. The funnel cap is configured retain the collapsible medical device and the nosecone pin within the tapered interior volume of the loading funnel.

Embodiment 10 includes the device of embodiment 9, wherein the locking collar assembly includes: a split locking collar comprising a first collar half and a second collar half; and a locking collar removably coupled to distal portions of the first collar half and the second collar half, wherein the locking collar secures the first collar half and the second collar half to the loading funnel to define the loading channel.

Embodiment 11 includes the device of any of embodiments 9-10, wherein the tapered interior volume comprises an approximate conical shape.

Embodiment 12 includes the device of any of embodiments 9-11, wherein the loading funnel includes male threads formed at the distal end of the loading funnel.

Embodiment 13 includes the device of embodiment 12, wherein the funnel cap includes: female threads formed at a proximal end of the funnel cap, wherein the female threads are configured to engage the male threads of the loading funnel to secure the funnel cap to the loading funnel; and one or more fluid ports configured to allow fluid to flow into and out of an interior volume of the loading cap and the loading funnel.

Embodiment 14 includes the device of any of embodiments 9-13, wherein the connector of the retainer comprises female threads configured to engage male threads of the delivery device.

Embodiment 15 includes the device of any of embodiments 9-14, wherein the collapsible medical device is an expanding frame containing a heart valve.

Embodiment 16 includes the device of any of embodiments 9-15, wherein the device is configured to be maintained with a storage jar containing a preserving fluid.

Embodiment 17 is a method for storing medical devices and loading the medical devices onto delivery devices, The method includes washing, with a sterile solution, a collapsible medical device that is stored within a tapered interior volume of a loading device in a partially collapsed state. The method also includes coupling a delivery device to a retainer positioned within the loading device. The retainer maintains the collapsible medical device within the loading device in the partially collapsed state prior to connection to the delivery device. Additionally, the method includes retracting the retainer through a loading channel of the loading device, where retracting retainer causes the collapsible medical device to move through the tapered interior volume to compress the collapsible medical device. The method includes removing the loading device from the delivery device. The method also includes sealing the collapsible medical device within the delivery device.

Embodiment 18 includes the method of embodiment 17, wherein washing the collapsible medical device includes: connecting a fluid delivery device to a fluid port of the loading device; and engaging the fluid delivery device to flow the sterile fluid into the loading system.

Embodiment 19 includes the method of any of embodiments 17-18, wherein washing the collapsible medical device includes submerging the loading system within bath comprising the sterile fluid, wherein the loading system comprises one or more fluid ports configured to allow the sterile fluid to flow into and out of the loading device.

Embodiment 20 includes the method of any of embodiments 17-19, wherein sealing the collapsible medical device within the delivery device comprises attaching a nosecone to a nosecone pin coupled to the retainer.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:
1. A loading device for loading a medical device onto a delivery device, the loading device comprising:
 a loading funnel configured to store a collapsible medical device within a tapered interior volume of the loading funnel in a partially collapsed state wherein the tapered interior volume decreases in volume from a first end of the loading funnel to a second end of the loading funnel;
a funnel cap coupled to the first end of the loading funnel;
a nosecone pin extending through the loading funnel; and
a medical-device retainer coupled to a proximal portion of the nosecone pin, the medical-device retainer configured to retain the collapsible medical device on a delivery device.

2. The loading device of claim 1, further comprising a cap coupled to the second end of the loading funnel, wherein the cap, the loading funnel, and the funnel cap form a closed volume configured to receive fluid for storage of the collapsible medical device therein.

3. The loading device of claim 2, wherein the funnel cap comprises a fluid chamber adjacent the loading funnel when coupled the first end of the loading funnel, and a fluid port configured to enable fluid to be injected into and/or extracted from the closed volume.

4. The loading device of claim 2, wherein the loading funnel comprises male threads at the second end of the loading funnel, wherein the male threads are configured to engage female threads of the cap.

5. The loading device of claim 4, wherein the loading funnel comprises male threads at the first end of the loading funnel, and wherein the funnel cap comprises female threads configured to engage the male threads at the first end of the loading funnel to secure the funnel cap to the loading funnel.

6. The loading device of claim 1, wherein the nosecone pin includes threads at a distal end thereof configured to couple to threads of a nosecone of a delivery device.

7. The loading device of claim 1, wherein the medical-device retainer includes threads at a proximal end thereof configured to couple to threads of a shaft of a delivery device.

8. The loading device of claim 1, wherein the funnel cap includes an opening for enabling fluid to enter and/or leave the interior volume of the loading funnel.

9. The loading device of claim 1, further comprising a locking collar assembly coupled to the second end of the loading funnel, wherein the locking collar assembly includes a loading channel, wherein the medical-device retainer is disposed within the loading channel and the medical-device retainer is coupled to the loading funnel via the locking collar assembly.

10. The loading device of claim 9, further comprising a cap coupled to the second end of the locking collar assembly, wherein the cap, the locking collar assembly, the loading funnel, and the funnel cap form a closed volume configured to receive fluid for storage of the collapsible medical device therein.

11. The loading device of claim 10, wherein the funnel cap comprises a fluid chamber adjacent the loading funnel when coupled to the first end of the loading funnel, and a fluid port configured to enable fluid to be injected into and/or extracted from the closed volume.

12. The loading device of claim 9, wherein the locking collar assembly comprises:
a split locking collar comprising a first collar half and a second collar half; and
a locking collar removably coupled to the first collar half and the second collar half, wherein the locking collar secures the first collar half and the second collar half together and to the loading funnel to define the loading channel.

13. A storage and loading assembly comprising:
a collapsible medical device;
a loading funnel, wherein in a storage configuration the collapsible medical device is partially collapsed within a tapered interior volume of the loading funnel, wherein the tapered interior volume decreases in volume from a first end of the loading funnel to a second end of the loading funnel;
a funnel cap coupled to the first end of the loading funnel;
a nosecone pin extending through the loading funnel; and
a medical-device retainer coupled to a proximal portion of the nosecone pin and coupled to the collapsible medical device, the medical-device retainer configured to be coupled to a delivery device.

14. The assembly of claim 13, further comprising a cap coupled to the second end of the loading funnel, wherein the cap, the loading funnel, and the funnel cap form a closed volume configured to receive fluid for storage of the collapsible medical device therein.

15. The assembly of claim 14, wherein the funnel cap comprises a fluid chamber adjacent the loading funnel when coupled to the first end of the loading funnel, and a fluid port configured to enable fluid to be injected into and/or extracted from the closed volume.

16. The assembly of claim 13, wherein the funnel cap includes an opening for enabling fluid to enter and/or leave the interior volume of the loading funnel.

17. The assembly of claim 13, further comprising a locking collar assembly coupled to the second end of the loading funnel, wherein the locking collar assembly includes a loading channel, wherein the retainer is disposed within the loading channel and the retainer is coupled to the loading funnel via the locking collar assembly.

18. The assembly of claim 17, further comprising a cap coupled to the second end of the locking collar assembly, wherein the cap, the locking collar assembly, the loading funnel, and the funnel cap form a closed volume configured to receive fluid for storage of the collapsible medical device therein.

19. The assembly of claim 18, wherein the funnel cap comprises a fluid chamber adjacent the loading funnel when coupled to the first end of the loading funnel, and a fluid port configured to enable fluid to be injected into and/or extracted from the closed volume.

20. The assembly of claim 17, wherein the locking collar assembly comprises:
a split locking collar comprising a first collar half and a second collar half, and
a locking collar removably coupled to the first collar half and the second collar half, wherein the locking collar secures the first collar half and the second collar half together and to the loading funnel to define the loading channel.

21. A method for storing medical devices and loading the medical devices onto delivery devices, the method comprising:
partially collapsing a collapsible medical device within a loading funnel, the loading funnel having a tapered interior volume that decreases in volume from a first end of the loading funnel to a second end of the loading funnel;
coupling a funnel cap to the first end of the loading funnel;
coupling a distal end of a nosecone pin to the funnel cap;
coupling a retainer to a proximal portion of the nosecone pin and to the collapsible medical device; and
filling the tapered interior volume of the loading funnel with a preservative liquid.

22. The method of claim 21, further comprising coupling a cap to a the second end of the loading funnel, wherein the cap, the loading funnel, and the funnel cap define a closed volume, wherein filling the tapered interior volume of the loading funnel with a preservative fluid comprises filling the closed volume with a preservative fluid.

23. The method of claim 21, wherein filling the tapered interior volume of the loading funnel with a preservative fluid comprises placing the loading funnel with the collapsible medical device partially collapsed within the tapered interior volume within a jar including the preservative fluid.

* * * * *